(12) United States Patent
Hama et al.

(10) Patent No.: US 7,758,224 B2
(45) Date of Patent: *Jul. 20, 2010

(54) LIGHT EMITTING DEVICE

(75) Inventors: Atsutomo Hama, Anan (JP); Tomotaka Honda, Anan (JP); Shinichi Nagahama, Tokushima (JP); Junji Takeichi, Anan (JP); Yoshinori Murazaki, Komatsushima (JP); Hiroto Tamaki, Anan (JP); Yukihiro Hayashi, Tokushima (JP)

(73) Assignee: Nichia Corporation, Anan-shi (JP)

( * ) Notice: Subject to any disclaimer, the term of this patent is extended or adjusted under 35 U.S.C. 154(b) by 383 days.

This patent is subject to a terminal disclaimer.

(21) Appl. No.: 11/662,803

(22) PCT Filed: Sep. 28, 2005

(86) PCT No.: PCT/JP2005/017823

§ 371 (c)(1),
(2), (4) Date: Mar. 14, 2007

(87) PCT Pub. No.: WO2006/038502

PCT Pub. Date: Apr. 13, 2006

(65) Prior Publication Data

US 2008/0089089 A1    Apr. 17, 2008

(30) Foreign Application Priority Data

Oct. 1, 2004   (JP) .............................. 2004-289653
Feb. 8, 2005   (JP) .............................. 2005-031992
Mar. 24, 2005  (JP) .............................. 2005-085600
May 27, 2005   (JP) .............................. 2005-154899

(51) Int. Cl.
*H01L 33/00*    (2010.01)

(52) U.S. Cl. .................... 362/555; 362/551; 362/84; 362/231

(58) Field of Classification Search ......... 362/572–574, 362/84, 293, 34, 551, 583; 385/901
See application file for complete search history.

(56) References Cited

U.S. PATENT DOCUMENTS 3,920,980 A * 11/1975 Nath .......................... 362/582

(Continued)

FOREIGN PATENT DOCUMENTS

JP        H03-43805 U        4/1991

(Continued)

OTHER PUBLICATIONS

The extended European Search Report of corresponding European Application No. 05788370.4, dated Jan. 27, 2010.

*Primary Examiner*—Sandra L O'Shea
*Assistant Examiner*—Danielle Allen
(74) *Attorney, Agent, or Firm*—Global IP Counselors, LLP

(57) ABSTRACT

A light emitting device, comprises: an excitation light source that emits excitation light; a wavelength conversion member that absorbs the excitation light emitted from the excitation light source, converts its wavelength, and releases light of a predetermined wavelength band; a light guide in which the center part (core) of its cross section has a refractive index that is higher than the refractive index of the peripheral portion (cladding), and which guides the light emitted from the wavelength conversion member to the outside; and wherein the wavelength conversion member is produced by laminating a plurality of layers that wavelength-convert different wavelengths of light.

20 Claims, 14 Drawing Sheets

U.S. PATENT DOCUMENTS

| | | | |
|---|---|---|---|
| 4,279,245 A * | 7/1981 | Takagi et al. | 600/139 |
| 4,329,737 A * | 5/1982 | Triller et al. | 362/555 |
| 4,415,240 A * | 11/1983 | Nishioka et al. | 385/33 |
| 5,003,434 A * | 3/1991 | Gonser et al. | 362/572 |
| 5,986,704 A * | 11/1999 | Asai et al. | 348/340 |
| 6,155,699 A | 12/2000 | Miller et al. | |
| 6,496,718 B1 * | 12/2002 | Lonky | 600/476 |
| 6,790,175 B1 * | 9/2004 | Furusawa et al. | 600/128 |
| 7,356,054 B2 * | 4/2008 | Hama et al. | 372/21 |
| 7,422,356 B2 * | 9/2008 | Hama et al. | 362/574 |
| 7,433,115 B2 * | 10/2008 | Hama et al. | 359/326 |
| 2002/0084748 A1 | 7/2002 | Ayala et al. | |
| 2004/0141336 A1 * | 7/2004 | West et al. | 362/555 |
| 2005/0031281 A1 * | 2/2005 | Nath | 385/125 |
| 2005/0139851 A1 * | 6/2005 | Sato | 257/99 |

FOREIGN PATENT DOCUMENTS

| | | |
|---|---|---|
| JP | H10-216085 A | 8/1998 |
| JP | 2000-326786 A | 11/2000 |
| JP | 2002-42526 A | 2/2002 |
| JP | 2002-95634 A | 4/2002 |
| JP | 2003-180614 A | 7/2003 |
| JP | 2004-71357 A | 3/2004 |
| WO | WO-01/40702 A1 | 6/2001 |
| WO | WO-02/101289 A2 | 12/2002 |

* cited by examiner

LIGHT EMITTING DEVICE

TECHNICAL FIELD

The present invention relates to a light emitting device mainly having an excitation light source, a wavelength conversion member, and a light guide.

BACKGROUND ART

Conventionally, endoscope devices for in vivo observations and for performing treatment during observations, and fiber scopes for observing in extremely narrow or dark spaces have been widely used.

Endoscopes and fiber scopes are constructed with extremely minute light guides and are able to illuminate spaces or the like such as inside body cavities like the stomach or other gaps or the like because the fibers transfer light which has been radiated from a light source.

In order to efficiently illuminate using minute fibers, the light source is required high brightness. Furthermore, when observing and in some cases diagnosing an affected area of an organ or within cavities, accurate reproduction of color information is important. Thus, the light source for endoscopes and fiber scopes require light which is close to natural light.

Further, in order to shorten the time a patient has to wait after the light source of an endoscope is turned on, it is necessary to use a light source of extremely high reliability so that the light will instantly come on and stabilize, and will not go out during use.

Examples of light sources that have been used in such applications include xenon lamps and metal halide lamps.

However, problems encountered with a xenon lamp or a metal halide lamp are that a vivid color cannot be achieved, it takes a long time for the color of the emitted light to stabilize, and the light cannot be instantly turned back on, among others.

Consequently, it has been proposed that a light emitting diode element (LED), laser diode element (LD), or other such semiconductor light emitting element be used instead of a xenon lamp or the like as the light source (see patent document 1, for example).

As shown in FIG. 17, a conventional endoscope device 100 is made up primarily of an image processing signal component 101 and an endoscope insertion component 102, and a white light source 111 equipped with a red semiconductor laser 111a, a green semiconductor laser 111b, and a blue semiconductor laser 111c is mounted in an illumination unit 110 in the image processing signal component 101. The semiconductor lasers 111a to 111c emit light in multi-vertical mode having a spectrum distribution with little interference and a plurality of wavelengths λ, and white light is obtained by mixing light of the three primary colors. The light emitted from this illumination unit 110 is guided by a light guide 103 to the endoscope insertion component 102.

A semiconductor light emitting element is small in size, has good electrical power efficiency, and emits light of vivid color. Also, because this element is formed from a semiconductor, there is no worry about burnt-out bulbs or the like. Furthermore, the initial drive characteristics are excellent, and such an element stands up well to vibration and to being repeatedly switched on and off. In particular, a semiconductor laser has far higher emission intensity than a light emitting diode, and therefore can be used as a light source with high luminance.

Patent Document Japanese Laid-Open Patent Application 2002-95634

DISCLOSURE OF THE INVENTION

Problems to be Resolved by the Invention

Nevertheless, a semiconductor laser has a narrower half band width than a light emitting diode, so a problem with a conventional endoscope device in which the white light source 111 comprised the red semiconductor laser 111a, the green semiconductor laser 111b, and the blue semiconductor laser 111c was that differences in the intensity of the various semiconductor lasers resulted in variance in the color tones, and this led to poor color reproducibility.

Also, because at least three kinds of semiconductor laser were required with a conventional endoscope device, the output of each semiconductor laser had to be controlled to obtain a specific white light, and adjusting this control proved difficult.

Furthermore, a semiconductor laser has a narrower angle of visibility than a light emitting diode, and its emission intensity is extremely high in the front direction, so a another problem is that even with white light, the color tone can vary due to slight misalignment of the various semiconductor lasers.

In addition, the necessary high level of color rendering has yet to be attained with a conventional endoscope device.

Means of Solving the Problems

According to the present invention, a light emitting device is obtained that has high illumination efficiency, (2) extremely little color tone variance, and that (3) emitted light with excellent color reproducibility, and/or (4) has good color rendering properties.

That is, a light emitting device of the present invention mainly comprises an excitation light source that emits excitation light; a wavelength conversion member that absorbs the excitation light emitted from the excitation light source, converts its wavelength, and releases light of a predetermined wavelength band; a light guide in which the center part (core) of its cross section has a refractive index that is higher than the refractive index of the peripheral portion (cladding), and which guides the light emitted from the wavelength conversion member to the outside; and wherein (1) the wavelength conversion member is produced by laminating a plurality of layers that wavelength-convert different wavelengths of light (see FIGS. 2a and b, Example 11).

Also, other light emitting device of the present inventions mainly comprises an excitation light source that emits excitation light; a wavelength conversion member that absorbs the excitation light emitted from the excitation light source, converts its wavelength, and releases light of a predetermined wavelength band; a light guide in which the center part (core) of its cross section has a refractive index that is higher than the refractive index of the peripheral portion (cladding), and which guides the excitation light emitted from the excitation light source to the wavelength conversion member; and further comprising one or more (2) to (8) as follows;

(2) the wavelength conversion member is produced by laminating a plurality of layers that convert different wavelengths of light (see FIGS. 1, 2a and b, Examples 2, 4, or the like), (3) the light guide distal end member is formed from a material that reflects the excitation light and/or the light that has undergone wavelength conversion (see FIGS. 1, 3a and b, Example 12), (4) the light guide is such that the diameter of the center part (core) of its cross section is formed larger only at the end on the wavelength conversion member side (see FIGS. 1, 13a and b, Example 13), (5) a wavelength-converted light reflecting film is provided to the portion of the wavelength conversion member into which the excitation light is guided, and/or an excitation light reflecting film is provided to the portion of the wavelength conversion member from which wavelength-converted light is guided (see FIGS. 1, 3a to d, Example 14), (6) an scatter preventing member is positioned between the wavelength conversion member and the light guide, and/or on the surface of the wavelength conversion member except for the portion from which wavelength-converted light is guided to the outside (see FIGS. 1, 4f to k 5l to o, Example 15), (7) the light guide is a plurality of light guides (see FIGS. 1, 9 to 12, Examples 5 to 8 or the like, (8) a light guide distal end member that supports one end of the light guide is comprised, and the wavelength conversion member, along with the end of the light guide, covers all or part of the end of the light guide distal end member (see FIGS. 1, 3a to e, 4f to k 5l to o, Example 9).

The light emitting device of the present invention is made up of at least an excitation light source, a wavelength conversion member, and a light guide, so the excitation light emitted from the excitation light source is guided to the emission portion, and the excitation light emitted from the emission is guided out to the light guide. The excitation light is guided out to the output portion (the other end) while repeatedly undergoing total reflection within the light guide. The excitation light that is guided out is directed at the wavelength conversion member provided to the output portion, and at least part of the excitation light is absorbed and its wavelength converted by the wavelength conversion member, becoming light of a specific wavelength band that is released and diffused. This light is guided to the outside. Alternatively, light whose wavelength has been converted by a fluorescent substance and excitation light that has passed through the wavelength conversion member without being absorbed are mixed and then guided to the outside.

This allows the desired light, such as white light, to be obtained with one or more excitation light sources. Also, since the desired light can be obtained with just one excitation light source, there is less variance in the color tone, and a light emitting device with excellent color reproducibility can be obtained.

Furthermore, a light emitting device with a wider divergence angle than when just an excitation light source is used can be obtained by using a combination of an excitation light source and a wavelength conversion member. Moreover, light of the specific wavelength can be color mixed more easily, and light with better color rendering can be obtained.

Also, since the excitation light source and the wavelength conversion member can be separated from one another by the light guide, the wavelength conversion member will not be directly exposed to heat produced by the excitation light source, high-intensity light, or the like, which prevents the deterioration of the wavelength conversion member and allows good-quality light to be obtained over an extended period without any change. Furthermore, the light guide makes it possible to freely set the illumination location without having to move the excitation light source. In addition, since no electricity flows to the light guide, there is no problem with current leakage or the like, so the device can be used more safety. Also, if the wavelength conversion member is disposed at a location where the light emitted from the wavelength conversion member will be guided through the light guide to the outside, then the excitation light source will be separated from the place where the light is released, so regardless of where the light is installed, it can be used even in places where the distal end of the light guide is soiled, and the excitation light source and/or the wavelength conversion member can be replaced more easily. Furthermore, the light generated by the excitation light source can be transferred to substantially all of the wavelength conversion member without attenuation, so the wavelength of the excitation light can be efficiently converted while the specific output state is maintained, making it possible to obtain the desired light at high emission efficiency.

Figure 1:
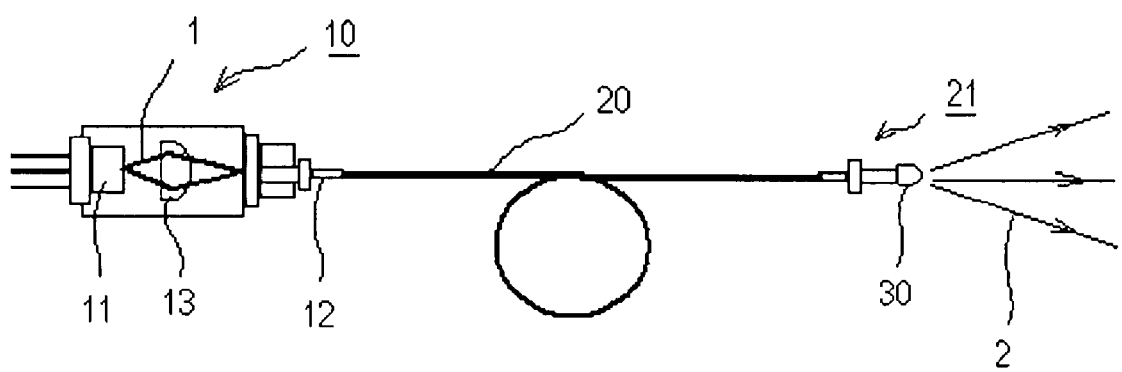
FIG. 1 is a simplified diagram illustrating an embodiment of the light emitting device of the present invention.

DESCRIPTION OF THE SIGN 1 excitation light
2 light
3 reflected light
10 excitation light source
11 light emitting element
12 emission portion
13 lens 20, 120 light guide
20a, 120a core
20b, 120b clad
21 output portion
30 wavelength conversion member
40 image capture component
41 image signal processor
42 camera
43 cable
50 subject
60 excitation light source unit
70 light guide distal end member
71 wavelength-converted light reflecting film
72 excitation light reflecting film
73 scatter preventing member
74 scattering member
75 cap
75b lens
76,76b support member

BEST MODE FOR CARRYING OUT THE INVENTION

With the light emitting device of the present invention, in particular, when the wavelength conversion member is formed from a plurality of layers that convert light into different wavelengths, suitable wavelength conversion can be successively carried out according to the wavelength of the incident light, and as a result, all of the light that is supposed to be converted does indeed undergo wavelength conversion, making more efficient wavelength conversion possible.

When the light guide distal end member is formed from a material that reflects the excitation light and/or the light that has undergone wavelength conversion, even if excitation light emitted from the light guide or light that has undergone wavelength conversion should be reflected back to the light guide side, the excitation light and/or wavelength-converted light can be effectively taken out to the outside by reflecting it again with the light guide distal end member, and this boosts the output.

When the light guide is such that the diameter of the center part (core) of its cross section is formed larger only at the end on the wavelength conversion member side, deterioration of the fiber itself at the light guide end can be prevented. Furthermore, since the optical density at the light guide end can be reduced, deterioration of the wavelength conversion member or the like that is disposed at the light guide end can be prevented, and light can be efficiently directed at the wavelength conversion member.

When a wavelength-converted light reflecting film is provided to the portion of the wavelength conversion member into which wavelength is guided, and/or an excitation light reflecting film is provided to the portion of the wavelength conversion member from which wavelength-converted light is guided, the light whose wavelength has been converted by the wavelength conversion member can be prevented from returning to the excitation light incident side, and any light that does return to the excitation light incident side can be reflected and taken out to the outside more efficiently. Furthermore, it is possible to prevent the excitation light from shining directly on the outside, and the excitation light from leaking from portions where it is not intended to be, for example. Therefore, emission efficiency can be further increased.

When an scatter preventing member is formed between the wavelength conversion member and the light guide, and/or on the surface of the wavelength conversion member except for the portion from which wavelength-converted light is guided to the outside, excitation light and/or wavelength-converted light can be prevented from diffusing in unintended directions.

When a plurality of light guides is provided, the output of the light emitting device can be easily increased.

When a light guide distal end member that supports one end of the light guide is provided, and the wavelength conversion member, along with the end of the light guide, covers all or part of the end of the light guide distal end member, deterioration of the wavelength conversion member can be reduced and output increased.

The light emitting device of the present invention will now be described through reference to the drawings, but the light emitting device described below is intended to embody the technological concepts of the present invention, and does not limit the present invention to what follows. Unless otherwise specified, the dimensions, material, and shape of the constituent members, their relative disposition, and so forth are merely examples given for the sake of description, and should not be construed to limit the scope of the present invention. The size of the members shown in the drawings, their positional relationships, and so forth may in some cases be exaggerated in order to make the description more clear. Furthermore, the various elements that make up the present invention may be in a mode such that a plurality of elements are constituted by the same member, so that a single member functions as a plurality of elements, or conversely, the functions of a single member may be allocated over a plurality of elements.

As shown in FIG. 1, the light emitting device of the present invention primarily comprises an excitation light source 10, a light guide 20, and a wavelength conversion member 30.

Excitation Light Source

The excitation light source is a light source which emits excitation light and any light may be used so long as the light can excite a fluorescent material to be discussed later. The excitation light source may use a device which is an energy source for the semiconductor light emitting elements, lamps or the like, as well as electron beams, plasma, and EL or the like. Of these, the use of light emitting elements is preferable. Light emitting elements make possible compact light emitting devices with good power efficiency because the light emitting intensity is high. Furthermore, a light emitting device can be obtained which has excellent initial drive properties and is robust against vibration or repeated on-off switching. Light emitting elements may be light emitting diode elements (LED) or laser diode elements (LD) or the like, but of these, laser diode elements are preferable. These make possible light emitting devices which have extremely high light emitting output. For instance, a device which radiates light with a main light emitting peak wavelength of approximately 350 nm to 550 nm is preferable. Thereby, as will be discussed later, fluorescent materials with good wavelength conversion efficiency can be used, and as a result, a light emitting device with high light emitting output can be obtained while obtaining light with a variety of colors. Furthermore, degradation of the wavelength conversion member, which will be discussed later, can be prevented, and a light emitting device with long life and high reliability can be obtained.

The excitation light source is comprising the light emitting element 11 or the like, and is constructed such that the light radiated from the light emitting element 11 is guided from the radiating part 12 to the light guide 20, as shown in FIG. 1 for instance. Usually, a lens 13 also is established between the laser element 11 and the radiating part 12.

A light emitting element usually comprises a semiconductor layer laminated over a substrate.

In order to form a nitride semiconductor of good crystallinity with good productivity, this substrate is preferably a sapphire substrate whose main plane is a C plane, R plane, or A plane. It is also possible to use an insulating substrate such as spinel ($MgAl_2O_4$) whose main plane is a C plane, R plane, or A plane, or a material other than a nitride semiconductor that is possible to grow a nitride semiconductor and has been known in the past, such as SiC (including 6H, 4H, and 3C), ZnS, ZnO, GaAs, Si, GaN, or an oxide substrate that is lattice-matched to a nitride semiconductor, or the like. Also, the substrate may have an off-angle, in which case it is preferable to use one whose off-angle is stepped, as this will allow a base layer composed of gallium nitride to be grown with good crystallinity.

If a different substrate from a nitride semiconductor is used, after growing the nitride semiconductor (buffer layer, base layer, or the like) which forms the base layer prior to forming the element structure on the different substrate from a nitride semiconductor, the different substrate may be removed by a method such as polishing to make a nitride semiconductor (such as GaN) with a single substrate, or the different substrate may be removed after forming the element structure.

By forming a base layer comprising a buffer layer (low temperature growth layer) and/or a nitride semiconductor (preferably GaN) or the like on a different substrate, the growth of the nitride semiconductor which composes the element structure will be better, and light in the ultraviolet band can be efficiently emitted by the pn junctions made from these nitride semiconductors.

A non-monocrystalline layer grown at low temperature, such as GaN, AlN, or GaAlN, or the like may be used as a buffer layer.

ELOG (epitaxially laterally overgrowth) growth may be used for the base layer (growth substrate) established on the different substrate. For instance, this can be achieved by optionally growing a nitride semiconductor layer on the different substrate and forming (to be nearly perpendicular to the orientation flat surface of the substrate) thereon a mask field with a stripe configuration or the like using a protective film (such as $SiO_2$ or the like) onto which a nitride semiconductor is not easily grown as well as forming a no-mask field for growing the nitride semiconductor such that the nitride semiconductor layer is grown over this protective layer. By growing the nitride semiconductor from the no-mask field, the nitride semiconductor will also growth in the mask field so that a nearly flat semiconductor layer can be formed by selective growth, or in other words, because growth in the lateral direction will occur in addition to growth in the film thickness direction. Alternatively, the same can be achieved by forming an opening region in the nitride semiconductor layer which has been grown on the different substrate and forming a nitride semiconductor layer on the substrate which includes this opening region. As a result, nitride semiconductor growth will occur in the lateral direction from the side surface of the opening region, and therefore a nearly flat semiconductor layer can be formed.

The semiconductor layer formed on this substrate may be any type of semiconductor including BN, SiC, ZnSe, GaN, InGaN, InAlGaN, AlGaN, BAlGaN, and BInAlGaN or the like. Similarly, Si, Zn, or the like may be added as an impurity element to the above elements to make a center of light emission. In particular, nitride semiconductors, and especially Group III nitride semiconductors (such as nitride semiconductors containing Al and Ga, and nitride semiconductors containing In and Ga, $In_XAl_YGa_{1-X-Y}N$, $0 \leq X$, $0 \leq Y$, $X+Y \leq 1$) are more suitable as light emitting layer materials which can efficiently emit light in the band from the ultraviolet band to a visible short wavelength band (for instance blue) where fluorescent materials can efficiently become excited. Furthermore, some of the gallium nitride compound type semiconductor may be replaced with B or P. The emission light wavelength from the light emitting element obtained can be adjusted by appropriately setting the types of semiconductor and the mixing ratio thereof. For instance, depending on the composition of the active layer, light which has a main emission peak wavelength between approximately 350 to 550 nm and preferably between approximately 350 to 500 nm or 360 to 500 nm, and in particular, by changing the In content of the active layer, light which has a main emission peak wavelength within a range of 420 to 490 nm can be obtained.

The semiconductor layer may have a single layer, but homostructures having MIS junctions, PIN junctions, or PN junctions or the like, heterostructures, and double heterostructures are preferably used. Furthermore, a multilayer laminate structure or an super lattice structure are also acceptable, as are a single quantum well structure or a multiquantum well structure laminated as a thin film which generates quantum effects.

These semiconductor layers may be formed using a known technology such as Metal Organic Chemical Vapor Deposition (MOCVD), Hydride Vapor Phase Epitaxy (HVPE), or Molecular Beam Epitaxy (MBE) or the like. The film thickness of the semiconductor layer is not restricted in particular, and a variety of film thickness is can be used.

The semiconductor layer may have a laminate double heterostructure or the like with a first contact layer of n-type gallium nitride, a first clad layer of n-type aluminum gallium nitride, a multiquantum well structure active layer with a plurality of lamination layers consisting of a well layer of indium nitride aluminum gallium or InGaN and a barrier layer of aluminum nitride gallium or GaN, a second clad layer of p-type aluminum nitride gallium, and a second contact layer of p-type gallium nitride, in order.

Incidentally, nitride semiconductors have n type conductivity without being doped with impurities. If n-type nitride semiconductors are formed in order to increase the light emitting efficiency or the like, Si, Ge, Se, Te, or C or the like are preferably introduced, as appropriate, as the n-type dopant. On the other hand, when forming a p-type nitride semiconductor, doping with a p-type dopant such as Zn, Mg, Be, Ca, Sr, or Ba or the like is preferable. For instance, impurity concentrations of approximately $10^{15}$ to $10^{21}/cm^3$ and particularly $10^{17}$ to $10^{20}/cm^3$ at the contact layer are exemplified. A nitride semiconductor is difficult to change to a p-type semiconductor simply by doping with a p-type dopant, so after introducing the p-type dopant, preferably the resistance is further dropped by annealing in a furnace or by plasma irradiation or the like.

When an insulating substrate is used as the substrate, a light emitting element composed of a nitride semiconductor can be formed by exposing a first contact layer by etching from the surface side of a second contact layer, forming first and second electrodes over the first and second contact layers, respectively, and cutting this product into chips. Also, when an insulating substrate is removed, or when a conductive substrate is used, there is no need to etch from the surface side of the second contact layer to expose the first contact layer, and the second electrode may be formed on the surface of the second contact layer, and the first electrode on the back of the substrate.

In particular, if the second electrode is formed on the second contact layer, the second electrode is preferably formed on nearly the whole surface as an ohmic electrode. Furthermore, the second electrode is preferably adjusted the sheet resistance as $Rp \geq Rn$ in which $Rp$ is the sheet resistance of the second electrode and $Rn$ is the sheet resistance of the first contact layer, for instance the n-type contact layers. Normally, the n-type contact layer for instance is formed with a film thickness between 3 and 10 μm, and particularly between 4 and 6 μm, so the sheet resistance $Rn$ is estimated to be between 10 and 15 ohms/square, and therefore a thin film is preferably formed so that $Rp$ has a sheet resistance higher than this. Specifically, a range of 150 μm or more may be exemplified for the second electrode.

In this manner, when the p-type electrode and the n-type electrode have a relationship such that $Rp \geq Rn$, a p side pad electrode which has an extension conductor is preferably established on the p electrode in order to diffuse current across the whole p layer in order to efficiently emit the light from the whole active layer. Thereby the external quantum efficiency can be further increased. The shape of the extension conductor is not restricted in particular, and for instance may be linear, curved, lattice, branched, ancyroid, or mesh or the like. These configurations are preferable because the area which blocks the light can be reduced. The p side pad electrode has increased light shielding properties in comparison to the total area so the line width and length is preferably designed so that the light shielding effect is not stronger than the light emission enhancing effect.

Furthermore, the second electrode is preferably formed from a translucent material. For instance, a metallic or alloy single layer film or multilayer film which includes ITO, ZnO, $In_2O_3$, $SnO_2$, gold and one type element selected from platinum family elements may be exemplified. In particular, if the second electrode is formed from a multiple layer film or an alloy film made from a metallic or an alloy including at least one element selected from a group of gold and platinum family elements, and another type of element, the sheet resistance $Rp$ of the p electrode can be adjusted depending on the content of gold or platinum family elements included therein, and therefore the stability and reproducibility of the electrode can be improved. However, gold and platinum elements have high absorption values in the 300 to 550 nm wavelength band, so the transparency can be improved by reducing the content thereof. The relationship between $Rp$ and $Rn$ can be determined by the condition of the light intensity distribution when the light emitting element is emitting light.

The light emitting element may also be a semiconductor laser element in which a ridge strip is formed over an active layer, the active layer is sandwiched by guide layers, and a resonator end face is provided.

The structure as follows is exemplified, for instance. An n-type contact layer which is an n-type nitride semiconductor layer, a crack preventing layer, an n-type clad layer, and an n-type light guide layer are formed on the substrate described above over an optional buffer layer. Excluding the n-type clad layer, the other layers can be omitted depending on the element. The n-type nitride semiconductor layer must have a bandgap which is wider than the active layer at least in the region which contacts the active layer, and therefore a composition which contains aluminum is preferable. For instance, an n-type $Al_yGa_{1-y}N$ ($0 \leq y < 1$) layer (value of y may be different for each layer) may be exemplified. Each layer may be grown while doping with an n-type impurity and made to be n-type, or may be grown without doping and made to be n-type.

An active layer is formed over the n-type nitride semiconductor layer. The active layer preferably has an MQW structure wherein an $In_{x1}Al_{y1}Ga_{1-x-y}N$ well layer ($0 \leq x1 \leq 1$, $0 \leq y1 \leq 1$, $0 \leq x1+y1 \leq 1$) and an $In_{x2}Al_{y2}Ga_{1-x2-y2}N$ barrier layer ($0 \leq x2 \leq 1$, $0 \leq y2 \leq 1$, $0 \leq x2+y2 \leq 1$, $x1 > x2$) are repeatedly alternatingly layered an appropriate number of times in order of barrier layer/well layer/barrier layer. Normally barrier layers are on both sides of the active layer.

The well layer is formed undoped. On one hand, except for the final barrier layer adjacent to the p-type nitride semiconductor layer, all of the barrier layers are doped (preferably $1 \times 10^{17}$ to $1 \times 10^{19}/cm^3$), with an n-type impurity such as Si or Sn or the like, and the final barrier wall is grown undoped. Incidentally, p-type impurities such as Mg or the like from the adjacent p-type nitride semiconductor layer are diffused in the final barrier layer (for instance at a concentration of $1 \times 10^{16}$ to $1 \times 10^{19}/cm^3$). By doping n-type impurities into the barrier layers excluding the final barrier layer, the initial electron concentration in the active layer will be higher and electron injection efficiency to the well layers will also be higher, and the light emitting efficiency of the laser will be increased. On the other hand, the final barrier layer is closest to the p-type nitride semiconductor side and therefore does not contribute to injecting electrons to the well layer. Therefore, by not doping the final barrier layer with n-type impurities but rather essentially doping by diffusing p-type impurities from the p-type nitride semiconductor layer, the efficiency for hole injection into the well layer can be increased. Furthermore, by not doping the final barrier layer with n-type impurities, mixing of differing types of impurities in the barrier layer which reduces the mobility of the carrier can be prevented. When growing the final barrier layer, the growth may be performed while doping with p-type impurities such as Mg or the like at a concentration of $1 \times 10^{19}/cm^3$ or lower. In order to suppress the effect of decomposing the active layer which contains In by gas etching when growing the p-type nitride semiconductor, the final barrier layer is preferably formed to be thicker than the other barrier layers. For instance, a thickness between 1.1 and 10 times the other barrier layers is preferable and a thickness between 1.1 and 5 times the other barrier layers is more preferable.

A p-type electron containment layer, p-type light guide layer, p-type clad layer, and p-type contact layer are formed as a p-type nitride semiconductor layer on the final barrier layer. Except for the p-type clad layer, the other layers may be omitted depending on the element. The p-type nitride semiconductor layer must have a bandgap which is wider than the active layer at least in the region which contacts with the active layer, and therefore formulations which contain Al are preferable. For instance, a p-type $Al_zGa_{1-z}N$ ($0 \leq z < 1$) layer (Value of z may differ for each layer) may be exemplified. Thereby a so-called double heterostructure is formed. Furthermore, each layer may be grown while doping with a p-type impurity to make p-type, and diffusing p-type impurities from other adjacent layers to make p-type is also acceptable.

The p-type electron containment layer is made from a p-type nitride semiconductor with an Al mixing ratio higher than that of the p-type clad layer, and preferably is formulated from $Al_xGa_{1-x}N$ ($0.1 < x < 0.5$). Furthermore, p-type impurities such as Mg or the like have a high concentration and doping is preferably performed at a concentration of $5 \times 10^{17}$ to $1 \times 10^{19}/cm^3$. Therefore, the p-type electron containment layer can effectively contain electrons in the active layer, and the threshold value of the laser can be reduced. Furthermore, the p-type electron containment layer may be grown to a thin-film of approximately 30 to 200 Angstroms, and if thin, the film can be grown at temperatures lower than the p-type light guide layer or the p-type light clad layer. Therefore, by forming the p-type electron containment layer, decomposition of the active layer which contains In can be suppressed as compared to when directly forming the p-type light guide layer or the like on the active layer.

Furthermore, the semiconductor light emitting element may be a semiconductor laser element which has a ridge stripe being formed in partway to the p-type light guide layer, furthermore, a protective layer, p-electrode, n-electrode, p pad electrode and n pad electrode or the like may also be formed.

The lens may have any configuration so long as the light radiated from the laser element is collected to the incidence region of the light guide, and a plurality of lenses may be arranged in a line between the laser element and the radiating part. The lens may be formed from inorganic glass or plastic or the like, but of these inorganic glass is preferable. The excitation light radiated from the excitation light source can be collected and efficiently guided to the light guide by providing a lens between the excitation light source and the light guide such that the excitation light radiated from the excitation light source can be guided through the lens to the light guide.

Light Guide

The light guide transfers the light radiated from the excitation light source, for example, guides the light to the wavelength conversion member. The light guide is constructed to flexible so that the shape can be changed freely. For instance, bending around corners and curves is possible, so the light can be guided to any desired location. Therefore, so long as this property is possible, any material and construction may be used. In particular, guiding the light radiated from the excitation light source to the wavelength conversion member without damping is preferable from the viewpoint of energy efficiency.

The light guide may for instance be an extremely fine glass fiber which is used as a transfer path for light when transferring the light, and a combination of materials which have a high refraction index and materials which have a low refraction index, or materials which have high reflectivity may be used. Of these materials, double layer materials with a cross-section where the center region (core) is surrounded by a surrounding region (clad) are preferable, and a material where the refraction index of the core is higher than the refraction index of the clad is more preferable from the viewpoint that a light signal can be transferred without damping. The light guide preferably has a core which occupies a larger area than the clad, from the viewpoint of reducing light density at the end of the light guide. Furthermore, the light guide preferably has a small diameter clad from the viewpoint of preventing light from returning to the light guide. For instance, a core diameter of approximately 1000 μm or less and a clad diameter (including the core diameter) of approximately 1200 μm or less may be exemplified, but a core diameter of approximately 400 μm or less and a clad diameter (including the core diameter) of approximately 450 μm or less is preferable. Specifically, a ratio of core/clad=114/125 (μm) or 72/80 (μm) or the like may be exemplified.

The light guide may be either a monofiber or a multifiber, but a monofiber is preferable. Furthermore, either a single mode fiber or a multimode fiber may be used, but a multimode fiber is preferable.

The material of the light guide is not restricted in particular, and for instance may be quartz glass or plastic or the like. Of these, the core material is preferably constructed from pure silica (pure quartz). Thereby transmission losses can be suppressed.

Figure 13A:
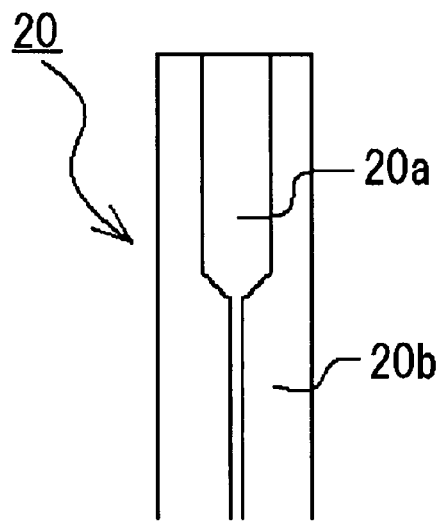
FIG. 13 is a cross-sectional diagram the light guide end portion in the light emitting device of the present invention
Figure 13B:
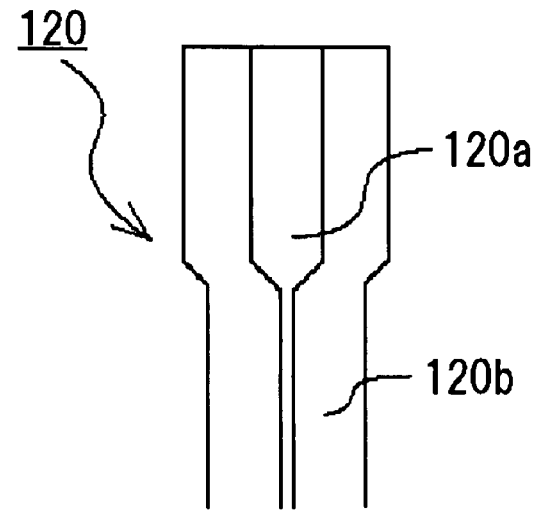

Furthermore, from the viewpoint of reducing light density at the light guide ends, as shown in FIGS. 13$a$ and $b$, the light guide may have a core diameter at the ends of the light guide 20, 120 which is wider than the core 20$a$, 120$a$ in the middle region, and for instance, a TEC fiber (clad 20$b$ diameter is fixed), or a taper fiber (clad 120$b$ diameter is tapered) or the like. Furthermore, photonic crystal fiber which has one or more air voids or air holes in the core or the clad (Refer to Osamu Toyama, "Photonics Crystal Fiber" Proceedings of 31st Meeting on lightwave Sensing Technology, LST 31-14, page 89-96, Jun. 6, 2003; Photonics Crystal Fiber DIAGUIDEORPCF, Mitsubishi Cable Industries, Ltd., Product Catalog, No. 6-184 (2003.01)) also known as index guiding, photonics bandgap, or hole assisted or the like, may also be used.

A photonics crystal fiber has its end covered with a specific member in order to keep moisture and the like from getting into air holes. Accordingly, light that has been transmitted to a light guide is released after spreading out wider than a core 220$a$ at the end. Examples of this are when the core diameter at the light guide end is about 1.05 to 2.0 times the core diameter in the center part, and when the light apparently spreads out as it is released from the light guide end. This prevents deterioration of the fiber itself at the light guide end. Furthermore, the optical density can be reduced at the light guide end, so deterioration of the wavelength conversion member or the like disposed at the light guide end can be prevented, and light can be directed uniformly and efficiently to the wavelength conversion member.

Even with an ordinary light guide whose core and/or cladding has a constant diameter, if the end is covered with a covering member, the light will come out wider at the light guide end than at the core, and the optical density can be reduced, just as with a photonics crystal fiber. There are no particular restrictions on the thickness or material of the covering member here, so long as the release of light is not impeded.

Wavelength Conversion Member

The wavelength conversion member absorbs part or all of the excitation light radiated from the excitation light source, converts the wavelength, and can emit light with a wavelength band longer than the excitation light from the laser elements and has a light emission spectrum containing for instance red, green, blue, as well as intermediary colors thereof such as yellow, blue green, and orange or the like. Therefore, the type of wavelength conversion member is not restricted in particular so long as the wavelength conversion member is constructed of materials which can achieve this function. In other words, the wavelength conversion member converts part or all of the light generated from the excitation light source to light which has a longer light emission peak wavelength, which is then emitted. In particular, even when the laser diode element is used as a light emitting element, visibility of a subject can be improved because the light is made broader emission spectrum having wide half bandwidth by this wavelength conversion member.

The wavelength conversion member is preferably constructed from material such that the light obtained from the wavelength conversion member can be white light regardless of the wavelength of the excitation light. Furthermore, in order to provide good light rendering properties, the wavelength conversion member is preferably constructed from a material where the average color rendering evaluation value (Ra) of the radiated light is 80 or higher.

Color rendering properties herein refers to the property of a certain light source to control the appearance of the colors of an object which is illuminated by that light source, and good light rendering properties generally refers to achieving close to the appearance of the colors of the object when illuminated by sunlight (Refer to Ohmsha Ltd., "Phosphor Handbook", p 429). Color rendering properties can be improved by using a fluorescent material layer to be discussed later in combination with a light emitting element. Furthermore, the average color rendering evaluation value (Ra) is basically determined by the value of the average color shift when 8 types of color indicators are illuminated by a test light source and a standard light source.

The color tone of the light obtained can be adjusted for instance by combining the light of the three primary colors (blue, green, red). Furthermore, the tone can also be adjusted by combining two colors of light which have a complementary color relationship such as blue and yellow, blue green and red, green and red, or blue-purple and yellow-green. Herein complementary colors refer to two colors which are on opposite sides of the white point of a color chart. Incidentally, the light of each of the colors used for adjusting the color tone is not all necessarily light which has the wavelength converted by the wavelength conversion member, and excitation light obtained from the excitation light source may also be used. Furthermore, with the present invention, the relationship between the color of light and the wavelength is in conformance with JIS Z8110.

The translucent member is transparent to the light from the light emitting element, but part of the light is absorbed without being transmitted, and is converted to heat. On the other hand, the light guide is fine enough to guide light and be flexible, so concentration of light and the associated heating will be significant at the translucent member or wavelength conversion member. Therefore, the present invention is extremely effective for constructions which use a light guide fine enough to be flexible which preferably has a clad diameter of 450 µm or less in order to alleviate the problems such as degradation by heat of the wavelength conversion member.

The wavelength conversion member is for instance constructed from a fluorescent material or the pigment or the like. In particular, a light emitting device which has excellent light emitting brightness and color rendering properties can be obtained by using fluorescent materials.

The fluorescent material is not restricted in particular so long as the material is excited by an excitation light from the excitation light source. Examples of various fluorescent materials include:

(i) alkali earth metal halogen apatite
(ii) alkali earth metal borate halogen
(iii) alkali earth metal aluminate
(iv) oxynitrides or nitrides
(v) alkali earth silicates and alkali earth nitride silicates
(vi) sulfides
(vii) alkali earth thiogallate
(viii) germanate
(ix) rare earth aluminate
(x) rare earth silicate
(xi) organic compounds and organic complexes or the like which are primarily activated by lanthanoids such as Eu.

These can be used one type and a combination of two types or more.

(i) Alkali earth metal halogen apatite fluorescent materials are preferably those which are primarily activated by lanthanoids such as Eu or transition metal elements such as Mn, such as $M_5(PO_4)_3X:RE$ (where M is one or more elements selected from Sr, Ca, Ba, Mg, and Zn; X is one or more elements selected from F, Cl, Br, and I; and RE is or more elements selected from lanthanoids and transition metals).

For instance, calcium chlorapatite (CCA) and barium chlorapatite (BCA) or the like may be exemplified, and specifically, $Ca_{10}(PO_4)_6Cl_2:Eu$, and $(Ba, Ca)_{10}(PO_4)_6Cl_2:Eu$ or the like may be exemplified.

(ii) Examples of alkali earth metal borate halogen fluorescent materials are $M_2B_5O_9X:RE$ (where M, X, and RE are defined as shown above) or the like.

For instance, calcium chlorborate (CCB) or the like may be exemplified, and specifically $Ca_2B_5O_9Cl:Eu$ or the like may be exemplified.

(iii) Examples of alkali earth metal aluminate fluorescent materials are europium activated strontium aluminate (SAE) and europium activated barium magnesium aluminate (BAM), as well as $SrAl_2O_4:R_E$, $Sr_4Al_4O_{25}:R_E$, $CaAl_2O_4:R_E$, $BaMg_2Al_{16}O_{27}:R_E$, and $BaMgAl_{10}O_{17}:RE$ (where RE is defined as shown above) or the like.

(iv) Oxynitride fluorescent materials are preferably those primarily activated by rare earth elements, and contain at least one Group II element and at least one Group IV element. Combinations of these elements are not restricted in particular, and examples include those expressed by the following formulations:

$$L_xJ_yO_zN_{((2/3)x+(4/3)y-(2/3)z)}: R \text{ or}$$

$$L_xJ_yQ_tO_zN_{((2/3)x+(4/3)y+t-(2/3)z)}:R$$

(where L is at least one type of Group II elements selected from a group consisting of Be, Mg, Ca, Sr, Ba, and Zn; J is at least one type of Group IV elements selected from a group consisting of C, Si, Ge, Sn, Ti, Zr, and Hf; Q is at least one type of Group III elements selected from a group consisting of B, Al, Ga, and In; R is at least one type of rare earth elements selected from a group consisting of Y, La, Ce, Pr, Nd, Sm, Eu, Gd, Tb, Dy, Ho, Er, Lu, Sc, Yb, and Tm; and $0.5<x<1.5$, $1.5<y<2.5$, $0<t<0.5$, and $1.5<z<2.5$.)

If x, y, and z in the equation are within the aforementioned ranges, high brightness will be obtained, and in particular, oxynitride fluorescent materials where x=1, y=2, and z=2 have higher brightness, and are more preferable. However, the above range is not a restriction and other materials may be used.

Specifically, oxynitride fluorescent materials which use alpha sialon as the base material, oxynitride fluorescent materials which use beta sialon as the base material, and Eu activated calcium aluminum silicon nitride expressed by the formula $CaAlSiN_3:Eu$ or the like may be exemplified.

Nitride fluorescent materials are preferably those activated by the rear rare elements. These fluorescent materials may be nitride fluorescent materials which include at least one type of the aforementioned Group II elements, at least one type of the aforementioned Group IV elements, and N, where B is within a range of 1 to 10,000 ppm. Alternatively, oxygen may also be included in the nitride fluorescent material formulation.

Of the aforementioned materials, nitride fluorescent materials containing Ca and/or Sr, Si, and N, such as calcium silicon nitride (CESN), strontium silicon nitride (SESN), and calcium strontium silicon nitride (SCESN), and particularly those activated by Eu and those where B is within a range of 1 to 10,000 ppm are preferable. A portion of the Eu may be replaced by at least one type of the aforementioned rare earth elements. A portion of the Ca and/or Sr may be replaced by at least one or more of the aforementioned Group II elements. A portion of the Si may be replaced by at least one type of the aforementioned Group IV elements.

Specifically, these nitride fluorescent materials are expressed by the equations $$L_xJ_yN_{(2/3)x+(4/3)y}:R \text{ or}$$

$$L_xJ_yO_zN_{(2/3)x+(4/3)y-(2/3)z}:R$$

(where L, J, and R are as defined above; and x, y, and z are such that $0.5 \leq x \leq 3$, $1.5 \leq y \leq 8$, and $0 \leq z \leq 3$), and B is preferably within a range of 1 to 10,000 ppm.

Examples of alkali earth silicates and alkali earth nitride silicates include $M_2Si_5N_8$:Eu,
$MSi_7N_{10}$:Eu,
$M_{1.8}Si_5O_{0.2}N_8$:Eu, and
$M_{0.9}Si_7O_{0.1}N_{10}$:Eu (where M is as defined above).

(vi) Examples of sulfites include alkali earth sulfides such as CaS:Eu and SrS:Eu or the like as well as $La_2O_2S$:Eu, $Y_2O_2S$:Eu, $Gd_2O_2S$:Eu, ZnS:Eu, ZnS:Mn, ZnCdS:Cu, ZnCdS:Ag/Al, ZnCdS:Cu/Al or the like.

(vii) Examples of alkali earth thiogallate include $MGa_2S_4$:Eu (where M is as defined above).

(viii) Examples of germanate include 3.5 MgO-0.5 $MgF_2$—$GeO_2$:Mn, and $Zn_2GeO_4$:Mn or the like.

(ix) Rare earth aluminates are preferably those primarily activated by lanthanoid elements such as Ce, for example yttrium aluminum garnet (YAG) and lutetium aluminum garnet (LAG), and specifically includes $Y_3Al_5O_{12}$:Ce, $(Y_{0.8}Gd_{0.2})_3Al_5O_{12}$:Ce, $Y_3(Al_{0.8}Ga_{0.2})_5O_{12}$:Ce, $(Y,Gd)_3(Al,Ga)_5O_{12}$:Ce, $Y_3(Al,Sc)_5O_{12}$:Ce, and $Lu_3Al_5O_{12}$:Ce (as well as those where all or part of Y is replaced by Lu and those where all or part of the Ce is replaced by Tb) as well as $Tb_3Al_5O_{12}$:Ce, and $Gd_3(Al,Ga)_5O_{12}$:Ce.

(x) Rare earth silicates include $Y_2SiO_5$:Ce, and $Y_2SiO_5$:Tb or the like.

(xi) Organic compounds and organic complexes are not restricted in particular, and any commonly known material may be used. Materials which are primarily activated by a lanthanoid element such as Eu or the like are preferable, but at least one type selected from a group consisting of the aforementioned rare earth elements as well as Cu, Ag, Au, Cr, Co, Ni, Ti, and Mn may be used in place of or in addition to Eu.

Of these materials, particularly preferable are: (ix) rare earth aluminate fluorescent materials primarily activated by lanthanoid elements such as Ce, specifically YAG type fluorescent materials expressed by the formulations $Y_3Al_5O_{12}$:Ce, and $(Y, Gd)_3Al_5O_{12}$:Ce or the like (including compounds where all or part of Y is replaced by Lu, and compounds where all or part of the Ce is replaced by Tb); and (iv) oxynitride and nitride fluorescent materials primarily activated by rare earth elements, specifically having a general formula of $$L_xJ_yN_{(2/3)x+(4/3)y}:R \text{ or}$$

$$L_xJ_yO_zN_{(2/3)x+(4/3)y-(2/3)z}:R$$

(where L, J, R, x, y, and z are as defined above).

Furthermore, particularly preferable are:
combinations of (ix) YAG together with at least one type of (i) CCA, (ii) CCB, and (iii) BAM;
combinations of (iii) SAE and (i) CCA: Mn;
combinations of (iii) SAE and (iv) SESN;
combinations of (iii) SAE and (iv) SCESN;
combinations of (iii) SAE and (iv) CESN;
combinations of (i) CCA, (ix) LAG, and (iv) SESN;
combinations of (i) CCA, (ix) LAG, and (iv) SCESN;
combinations of (i) CCA, (ix) LAG, and (iv) CESN;
combinations of (i) CCA, (ix) LAG, and (iv) $CaAlSiN_3$:Eu;
combinations of (ix) LAG, and (iv) SESN;
combinations of (ix) LAG, and (iv) SCESN;
combinations of (ix) LAG, and (iv) CESN; and
combinations of (ix) LAG, and (iv) $CaAlSiN_3$:Eu.

The nitride fluorescent materials are excited by ultraviolet light and light on the short wavelength side of visible light, and can emit light to the long wavelength side of visible light, and therefore have good color rendering properties. Further, the rare earth aluminate fluorescent materials have high heat durability and therefore can discharge stable light, and also have good wavelength conversion efficiency, and can therefore efficiently emit light. Furthermore, using a combination of these fluorescent materials is preferable. Therefore, light which has an average color rendering evaluation value (Ra) of for instance 80 or higher and which has good color rendering properties can be obtained.

As pigments, dyes and fluorescent dyes such as perylene or the like may be exemplified.

In order to prevent the formation of aggregates and to show maximum light absorbency and light converting efficiency, these fluorescent materials and pigments or the like normally have a particle size in the range of approximately 1 μm to 20 μm, and a range of approximately 2 μm to 8 μm is preferable, and a range of approximately 5 μm to 8 μm is more preferable. Furthermore, by using this type of fluorescent material which has a relatively large particle size, the productivity of the light emitting device can be improved. Herein, the particle size indicates the average particle diameter obtained using the air permeation method. Specifically, in an environment with a temperature of 25° C. and a humidity of 70%, a 1 cm$^3$ test sample is weighed, and after packing into a special tube shaped container, dry air at a fixed pressure is made to flow, and the relative surface area is determined from the pressure differential, and then the average particle size is calculated.

The wavelength conversion member in the present invention may be made up of just the above-mentioned fluorescent substance, etc., but if desired, it can also be mixed into a covering member along with a filler. This makes it easier to affix the wavelength conversion member to the light guide. Also, since the wavelength conversion member can be disposed uniformly, a light emitting device with less color unevenness can be obtained.

The covering member may for instance be an inorganic substance such as inorganic glass, yttria sol, alumina sol, or silica sol; or an organic substance such as one or more types of polyolefin resin, polycarbonate resin, polystyrene resin, epoxy resin, acrylic resin, acrylate resin, methacrylic resin (PMMA or the like), urethane resin, polyamide resin, polynorbornene resin, fluoridated resin, silicone resin, modified silicone resin, modified epoxy resin, as well as liquid crystal polymer or the like. These covering members preferably have excellent heat durability, light durability, weather durability, and transparency. Of these materials, fluoridated resin and silicone resin (particularly dimethylsiloxane and methyl polysiloxane resins) or the like are preferable.

If the wavelength conversion member is comprising a fluorescent material or the like and a resin which is a covering member, the weight ratio of the fluorescent material or the like and the resin are mixed to be preferably within a range of approximately 0.5 to 10:1, and more preferably within a range of approximately 1 to 3:1, or 1.5 to 2.5:1. However, as will be described later, if the wavelength conversion member is formed with a laminate structure, the ratio of fluorescent material or the like and resin in each layer does not necessarily have to be the same. For instance, the material used and the ratios thereof may be appropriately adjusted in consideration of the heat durability, weather durability, and refractive index or the like of the fluorescent material as well as the properties of the actual resin or the like.

Filler is preferably a material which can reflect, disperse, and/or scatter or the like light which is illuminated from the outside. Thereby the excitation light can uniformly be illuminated onto the fluorescent material or the like, which will have the effect of reducing color variation. Examples of the filler include silica (fumed silica, sedimentary silica, fused silica, crystalline silica, ultrafine powdered amorphous silica, or silicic anhydride or the like), quartz, titanium dioxide, tin oxide, zinc oxide, tin monoxide, calcium oxide, magnesium oxide, beryllium oxide, aluminum oxide, boric nitride, silica nitride, alumina nitride and other metallic nitrides, SiC and other metallic carbides, calcium carbonate, potassium carbonate, sodium carbonate, magnesium carbonate, barium carbonate and other metallic carbonate, aluminum hydroxide, magnesium hydroxide and other metallic hydroxides, aluminum borate, barium titanate, calcium phosphate, calcium silicate, clay, gypsum, barium sulfate, mica, diatomic earth, white clay, inorganic balloon, talc, lithopone, zeolite, halloysite, fluorescent material, and metal shavings (silver powder) or the like. Furthermore, in order to achieve strength, needle shaped fillers such as potassium titanate, barium silicate, and glass fiber or the like may also be used. Of these, barium titanate, titanium oxide, aluminum oxide, and silicon oxide or the like are preferable.

The particle size of the filler is not restricted in particular, and for instance, filler where the median particle size is greater than 1 μm and less than 5 μm can readily diffusely reflected light from the fluorescent material, and can suppress color variation which easily occurs when using a large diameter fluorescent material or the like. Filler which has a median particle size greater than 1 nm and less than 1 μm will have a slightly lower effect on the light wavelength from the light emitting element, but can increase the viscosity of the covering member such as resin without reducing the luminosity. Therefore fluorescent material or the like can be nearly uniformly dispersed in the resin and be maintained in that condition, and therefore even when using relatively larger diameter fluorescent materials or the like which are difficult to handle, the material can be produced with good yields. When filler with a median particle size greater than 5 μm and less than 100 μm is included in the covering member such as resin, color variation of the light emitting element can be improved because of the effect of light scattering, and the thermal impact durability of the resin can be increased. Incidentally, the filler may have a variety of shapes such as spheres, needles, or flakes, in consideration of the scattering properties and reflection properties or the like.

The filler preferably has approximately the same particle size and/or shape as the fluorescent material or the like. Herein, approximately the same particle size means that the difference between the median particle size of each of the particles is less than 20%, and approximately the same shape means that the difference in the roundness value (roundness=circumferential length of a true circle equal to the projected surface area of the particle/circumferential length of the projection of the particle) which shows the degree of true roundness of each particle is less than 20%. By using this type of filler, the fluorescent material or the like and the filler will mutually interact so that the fluorescent material or the like will be thoroughly dispersed throughout the covering member such as resin, and color variation can be more positively suppressed.

The filler may for instance account for between 0.1 and 80 wt %, and particularly 70 wt % or less, 50 wt % or less, 40 wt % or less, or 30 wt % or less of the total wavelength conversion member.

The wavelength conversion member is made by mixing the aforementioned fluorescent material or the like together with optional filler in a resin which is the covering member, using an appropriate solvent if necessary, and can be formed to the desired shape by a method such as the potting method, spray method, screen printing method, stencil printing method or the like, as well as plastic molding methods such as the injection method, compression method, transfer method, projection method, extrusion method, lamination method, calendar method, and injection mold method or the like, vacuum coating method, powder spray coating method, electrostatic deposition method, and electric migration deposition method or the like. Furthermore, the fluorescent material or the like and the optional filler and an appropriate solvent can be mixed together, and using a forming method which pressurizes while optionally heating or electrodeposition or the like without using a covering member.

The wavelength conversion member may be formed as a single layer of one type of fluorescent material or the like, or may be formed as one layer of a uniform mixture of two or more types of fluorescent materials or the like, or may be laminated with two or more layers where each layer contains one type of fluorescent material or the like, or may be laminated with two or more layers where each layer contains a uniform mixture of two or more types of fluorescent materials or the like. For the case where two or more single layers are laminated, the fluorescent material or the like contained in each layer may convert the wavelength of the same wavelength of incident light to the same wavelength of radiated light, or may convert incident light with the same wavelength to radiated light with different wavelengths, but the wavelength conversion members preferably convert the wavelength of incident light with different wavelengths to radiation light with the same or different wavelengths. Thereby all of the light which is incident on the wavelength conversion member and is to be converted can have the wavelength converted, and more efficient wavelength conversion can be performed. For the case where two or more layers are laminated, each layer may be made through separated steps, and it may be two or more layers by using the difference of specific gravity between fluorescent materials.

Figure 2A:
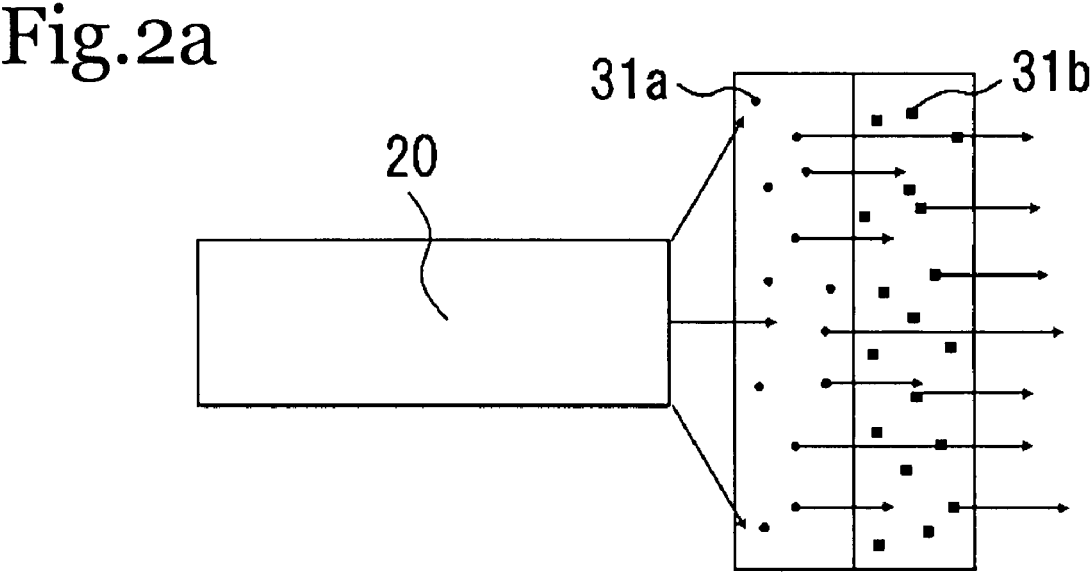
FIG. 2 is a simplified diagram illustrating the structure of the wavelength conversion member in the light emitting device of the present invention.
Figure 2B:
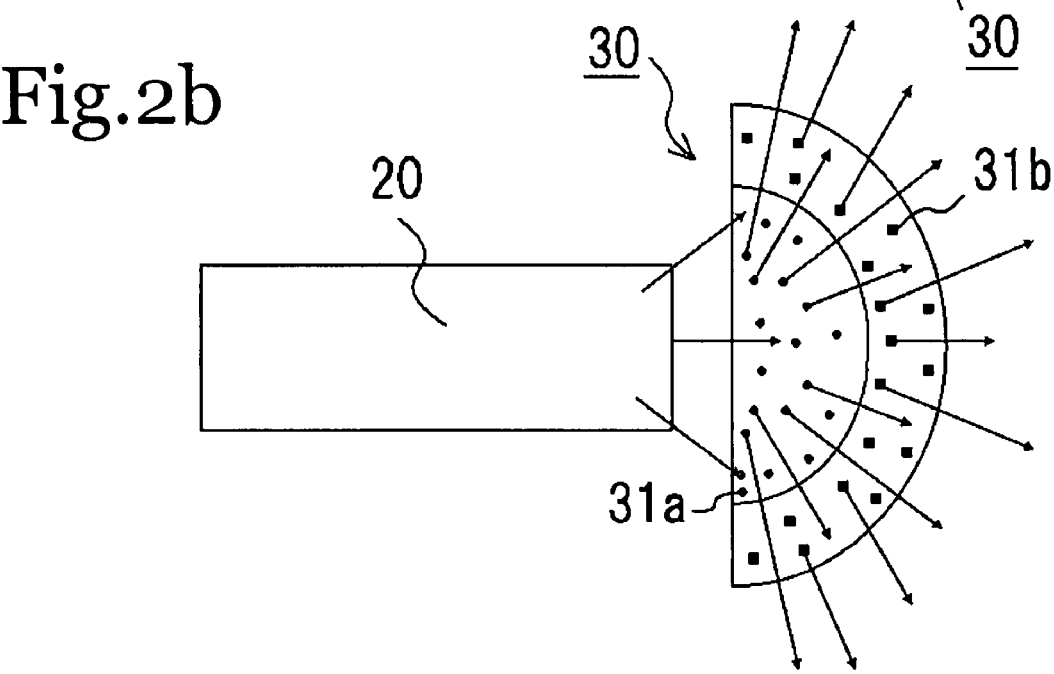

As shown in FIG. 2a, the wavelength conversion member 30 may comprise laminated sheets containing mutually different types of fluorescent substances 31a and 31b, or as shown in FIG. 2b, it may comprise a lamination configuration in which an upper layer containing the fluorescent substance 31b completely covers a lower layer containing the fluorescent substance 31a, which is different from the fluorescent substance 31b. There are no particular restrictions on the thickness of the wavelength conversion member, which can be suitably adjusted according to the materials used. For instance, when a fluorescent substance, a resin, or the like is formed as a thick film, conversion efficiency is improved and as a result the emission efficiency is higher, but on the other hand, the absorption of light and so forth lower emission efficiency, so the suitable film thickness is preferably selected by taking these factors into account.

As shown in FIG. 1, the wavelength conversion member 30 may be attached to the end of the light guide 20, or in other words the output region 21 in order to guide the excitation light 1, or may be attached to the connection part between the excitation light source 10 and the light guide 20 which is the radiating part 12 for the excitation light 1. The case of the latter may be used even in locations where the tip end of the light guide will get dirty. Furthermore, replacement of the translucent member or the wavelength conversion member will be simplified. Furthermore, productivity can be increased by establishing the translucent member or the wavelength conversion members in various locations.

Figure 4F:
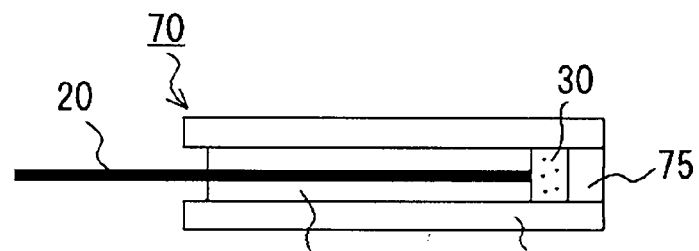
FIG. 4 is a simplified diagram illustrating the structure of another light guide distal end member in the light emitting device of the present invention.
Figure 4G:
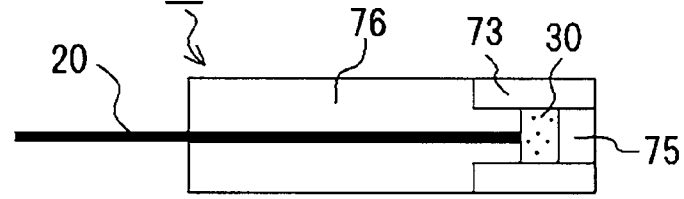
Figure 4H:
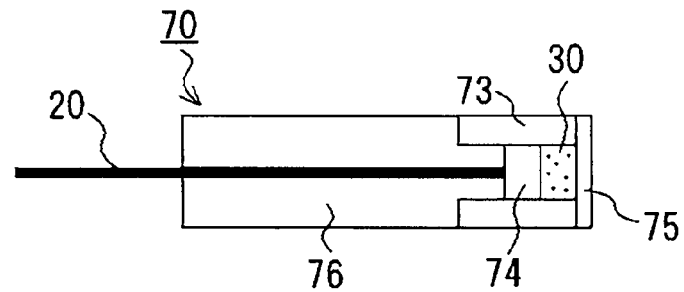
Figure 4I:
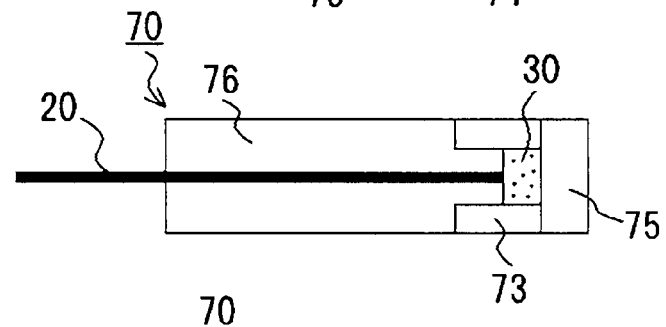
Figure 4J:
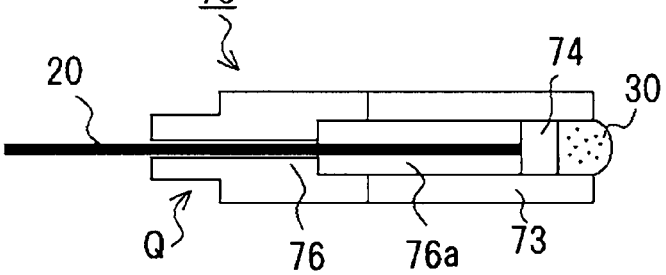

As shown in FIG. 4j, the wavelength conversion member 30 is preferably in the form of a bowl that protrudes from the emission side. This shape further increases brightness.

Also, if a fluorescent substance or the like is added to a lens provided to the excitation light source, then the lens itself may function as a wavelength conversion member. The lens function causes the wavelength-converted excitation light to be converged more reliably at the emission portion, so color variance can be eliminated, and since the wavelength conversion member can be manufactured by manufacturing the lens, the cost of manufacturing the wavelength conversion member can be reduced.

Furthermore, the wavelength conversion member may be provided to part of the interior of the light guide by having the core material contain a fluorescent substance or the like, for example.

Figure 3A:
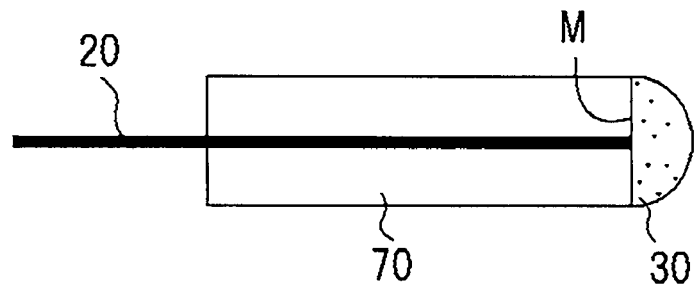
FIG. 3 is a simplified diagram illustrating the structure of the light guide distal end member in the light emitting device of the present invention.

The wavelength conversion member may also be formed so as to cover only the end (end face) of the light guide, but if the light emitting device is equipped with a light guide distal end member (discussed below), then as shown in FIG. 3a, it is preferable if part, or better yet all, of the end face of this light guide distal end member is covered, rather than just the light guide end. This results in the wavelength conversion member being formed over a wider region, which increases heat resistance, improves adhesion, and also prevents separation and so forth of the wavelength conversion member. Also, the density of the light illuminating the wavelength conversion member can be reduced, which makes it possible to prevent deterioration of the resin. Furthermore, this increases light take-off efficiency and allows a light emitting device with higher brightness to be obtained. In particular, the greater is the surface area over which the end of the light guide distal end member is covered by the wavelength conversion member, the better is this effect.

A concrete form of the wavelength conversion member of the present invention preferably uses a combination of $(Sr, Ca)_5(PO_4)_3Cl:Eu$ (blue emitted light) and LAG or $BaSi_2O_2N_2:Eu$ (green to yellow emitted light) and SCESN (red emitted light); or a combination of CCA, CCB, or BAM (blue emitted light) and YAG (yellow emitted light); or a combination of CCA, CCB, or BAM or the like (blue emitted light) and LAG (green emitted light) and SCESN (red emitted light) are preferably used, arranged in this order from the light incidence side. Therefore, when combined with a light emitting element which has a light emission peak wavelength within the short wavelength range of visible light from 360 to 470 nm, the light emitting efficiency can be further improved.

Further, a combination of LAG (green emitted light) and SESN, SCESN, $CaAlSiN_3:Eu$ (red emitted light) is preferably used. When combined with a light emitting element which has a light emission peak wavelength in the neighborhood of 450 nm (for instance 400 to 460 nm), the light emitting efficiency can be improved. Incidentally, the desired white light can be achieved from the various color light by changing the formulation ratios of the fluorescent materials used. In particular, if a combination of CCA or the like (blue emitted light) and YAG (yellow emitted light) is used, the weight ratio is preferably approximately 1 to 20:1, more preferably approximately 5 to 10:1, and thereby the light emitting efficiency can be increased.

Furthermore, if a fluorescent material which emits yellow light and a fluorescent material which emits red light are used in combination, and if combined with a light emitting element which has an emission peak wavelength in the neighborhood of 450 nm in the short wavelength band of visible light, the mixed color light which is obtained by combining the excitation light discharged from the light emitting elements and the light release from the fluorescent material will be guided externally as light from the wavelength conversion member. This light will white light with a redish hue.

Moreover, if a fluorescent material which emits green to yellow light is used, a light emitting element which has an emission peak wavelength in the neighborhood of 450 nm (440 to 470 nm), for instance 445 nm, a short wavelength band of visible light will preferably be used in combination. Therefore the light can be made to be white light by combining the excitation light from the light emitting element with yellow light converted from the excitation light. Also, absorption of the light during wavelength conversion can be avoided and the light emitting efficiency can be increased.

For the case where a combination of fluorescent material which emits blue light and fluorescent material which emits yellow light is used, by combining with a light emitting element which has an emission peak wavelength near 375 nm in the ultraviolet light band, the light released will be the white light being released from the wavelength conversion member. Ultraviolet light is invisible to human eyes so the only light will be the light released from the fluorescent material with a wavelength converted to visible light.

Furthermore, if (1) a light emitting element which has an emission peak wavelength around 400 nm (for instance 370 to 420 nm) in the short wavelength band of visible light is used in combination with (2) a fluorescent material which emits light closer to blue than the light emitting elements (for instance 440 to 460 nm), (3) a fluorescent material which emits green light (for instance 520 to 540 nm) when excited by blue light, (4) a fluorescent material which emits yellow light (for instance 550 to 580 nm) when excited by blue light, and (5) a fluorescent material which emits red light (for instance 640 to 660 nm) when excited by blue light, then the light release from the wavelength conversion member will primarily be white light. In particular, these fluorescent materials are preferably arranged in this order from the side of light incidence. With this combination, the light emitting efficiency can be increased. Furthermore, if a combination of (1), (2), and (4) is used, an even higher light emitting efficiency can be achieved. Furthermore, if a combination of (1) through (3) and (5) is used, the color rendering properties can be improved. Incidentally in these cases, excitation light from the light emitting element was not utilized as a color component of the light, and the white color was obtainable using only light which had been converted by the fluorescent material, so the color temperature and color coordinates were not changed by the light output from the light emitting element, and the white color intensity could be adjusted.

From another standpoint, when the wavelength conversion member is formed with a laminated structure, the configuration may be such that no fluorescent substance is contained in the layer closest to the side on which the light is incident (first layer), only a covering member is disposed, and the above-mentioned fluorescent substance or the like is contained in the second and subsequent layers. This lowers the optical density at the end of the wavelength conversion member, so deterioration of the second and subsequent layers can be reduced, and emission efficiency and emission output can be increased.

Also, the configuration may be such that a filler and/or a fluorescent substance that is not excited by excitation light and reflects excitation light is contained in the layer closest to the side on which the light is incident (first layer), and the above-mentioned fluorescent substance or the like is contained in the second and subsequent layers. This scatters the wavelength on the incident side of the wavelength conversion member, and reflects it on the emission side, allowing all of the wavelength-converted excitation light to be taken out more efficiently. Furthermore, the optical density of the excitation light can be further decreased in the first layer, so deterioration of the second layer can be reduced. This affords higher emission efficiency and emission output.

It is especially favorable if a second fluorescent substance contained in the second layer is excited by light from the excitation light source, and a first fluorescent substance contained in the first layer is excited by light from the second fluorescent substance. This more effectively reduces deterioration of the wavelength conversion member.

Furthermore, the configuration may be such that a fluorescent substance with high resistance to light and heat is contained in the layer closest to the side on which the light is incident (first layer), and the above-mentioned fluorescent substance is contained in the second and subsequent layers, regardless of the resistance to heat and light. In other words, the first layer having the first fluorescent substance and the second layer having the second fluorescent substance can be disposed in that order from the side closest to the excitation light source. Here, the first fluorescent substance preferably produces less heat than the second fluorescent substance when irradiated with excitation light. This reduces deterioration of the wavelength conversion member as a whole. Another layer can be interposed between the first and second layers. The heat produced by the first fluorescent substance and the second fluorescent substance may, for example, be determined by irradiating a first fluorescent substance and a second fluorescent substance of substantially equal volume with an excitation light source and comparing the heat generation temperature of each.

A translucent member composed of a covering member (wavelength conversion member) containing a fluorescent substance or the like was described above, but in the following case, it is possible to use a translucent member composed of a covering member or the like, without a fluorescent substance necessarily being required. That is, when the light guide distal end member is formed form a material that reflects the light from the light source, or when the light guide is such that the diameter of the center part (core) of its cross section is formed larger only at the end on the translucent member side, or when a light reflecting film is provided to the portion of the translucent member into which light is guided, or when an scatter preventing member is formed between the translucent member and the light guide and/or on the surface of the translucent member except for the portion from which wavelength-converted light is guided to the outside, or when a plurality of light guides are provided, or when the translucent member, along with the end of the light guide, covers all or part of the end of the light guide distal end member, the effect obtained will be basically the same as when using the wavelength conversion member discussed in the effect of the invention. In this Specification, a case of using a wavelength conversion member in which a fluorescent substance or the like was contained in a covering member as the translucent member was described in order to simplify description, but in these cases it is possible to replace the wavelength conversion member with a translucent member that does not contain a fluorescent substance or the like. When a translucent member that does not contain a fluorescent substance is used, the light source may be one that excites a fluorescent substance, that is, just an ordinary light source rather than an excitation light source. Therefore, in the various cases mentioned above, the excitation light source may be replaced with a light source that does not excite.

There are no particular restrictions on the translucent member as long as it is a material capable of transmitting light from the light source, but examples include the above-mentioned covering member alone, and this covering material containing the above-mentioned filler or the like. This allows the light obtained from the light source to be used directly, without first undergoing wavelength conversion, and allows the directivity of the light to be controlled. Also, adding a filler allows the light to be scattered before being taken out.

Light Guide Distal End Member

The end of the light guide, or in other words the end which is not connected to the excitation light source is preferably supported by a light guide distal end member. The radiating light from the light guide can easily be fixed by this light guide distal end member. Furthermore, depending on the material and shape thereof, the light emitting efficiency can be increased and the assembly of the light emitting device can be simplified. Therefore, the light guide distal end member may be constructed using any material and configuration so long as the light guide can be supported. As shown by Q in FIG. 4$j$, when a step is formed on the light guide side of the light guide distal end member, this step serves as a contact face that facilitates the fixing of a lighting device, for instance.

The light guide distal end member is preferably formed from a material which has high reflectivity towards the wavelength converted light and/or the excitation light, high refractive index for light, or high thermal conductivity, or a material which provides two or more of these characteristics. For instance, a material where reflectivity is 80% or higher at the peak wavelength of the wavelength converted light and/or the excitation light, the refractive index is n: 1.4 or higher for light in the 350 to 500 nm range, and/or the thermal conductivity is 0.1 W/m° C. or higher is preferable. Specific examples include Ag, Al, $ZrO_2$, borosilicate glass, stainless steel (SUS), carbon, copper, and barium sulfate or the like. Of these materials, if $ZrO_2$ is used the reflectivity will be high and machining for the light guide to pass through will be simple, but if stainless steel is used, the tensile strength can easily be maintained, and therefore forming with $ZrO_2$ or stainless steel (for instance SUS303 or the like) is preferable.

Furthermore, only the end surface of the light guide distal end member (the surface which is conform with end surface of the light guide, see M in FIG. 3$a$ for instance) preferably has a mirror for specular reflection or diffuse reflection, or may have a concave and convex shape for. Thereby if excitation light which has once been radiated from the light guide and/or light which has had the wavelength converted returns to the light guide side, the excitation light and the wavelength converted light can effectively be removed again by reflecting using the light guide distal end member, and therefore the optic output can be increased. Furthermore, if the end surface has a concave and convex shape, the adhesion of the wavelength conversion member to the light guide distal end member can be increased, thermal dissipation of the wavelength conversion member can be increased, and peeling or degradation of the wavelength conversion member can be prevented. Incidentally, a surface which has specular reflectivity and/or a concave and convex shape preferably is used not only for the light guide distal end member, but also for the light guide end surface.

The light guide distal end member may for instance have a cylindrical shape in order to cover the outer circumference of the light guide, and various functional films/members which provide various functions to the end surface of the light guide may be integrated with or attached separately thereto, or a cover or cap or the like which covers the end surface of the light guide as well as other functional films/members or the like may be integrated with or separately attached thereto. Incidentally, if the light guide distal end member has a cylindrical configuration, the diameter is for instance preferably 3 mm or less.

Figure 3B:
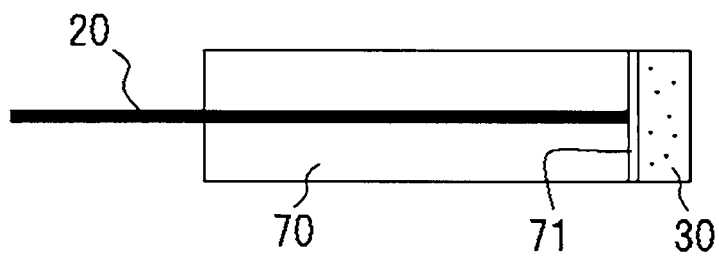
Figure 3C:
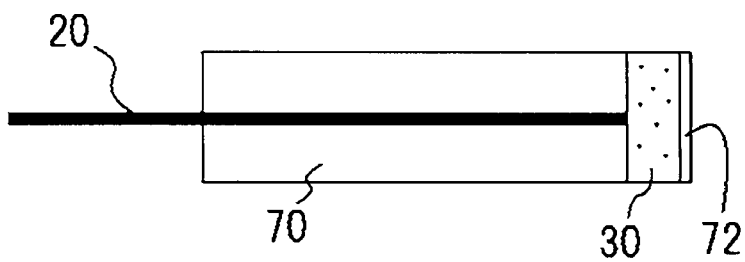
Figure 3D:
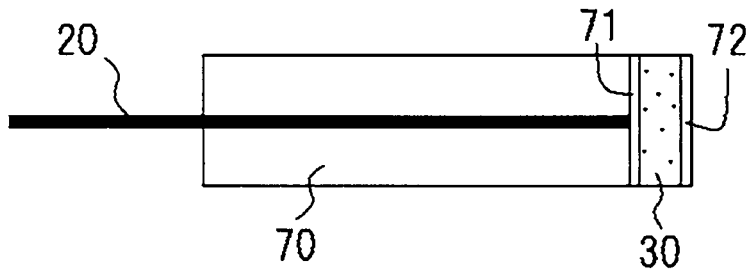
Figure 3E:
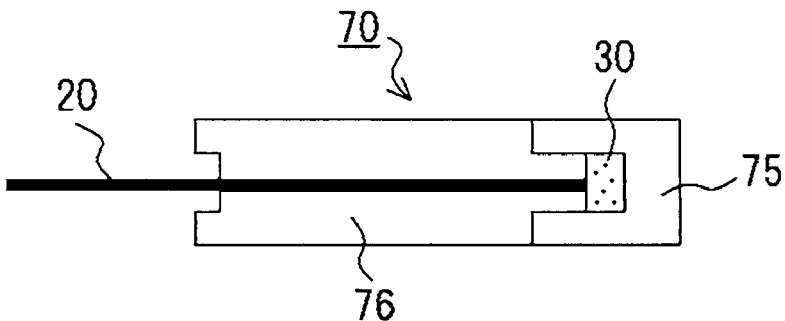

More specifically, examples include one in which the light guide distal end member 70 is cylindrical and the wavelength conversion member 30 is attached to the end thereof as shown in FIG. 3a; one in which various functional films (such as a wavelength-converted light reflecting film 71 or an excitation light reflecting film 72, which are discussed below) are attached to the light guide distal end member 70 as shown in FIGS. 3b to d; and one in which the light guide distal end member 70 is made up of one or more support members 76, 76a and one or more members, and some of these members are attached as functional films or functional members (such as an scatter preventing member 73 or scattering member 74, which are discussed below), cap 75, lens 75b or the like, as shown in FIG. 3e and FIGS. 4f to 5o. This prevents the separation of the wavelength conversion member, and improves the light take-out efficiency and directivity.

Figure 4K:
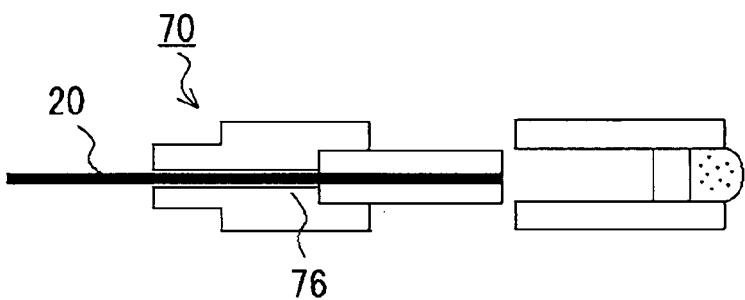

The light guide distal end member 70 can also be removable between the desired members, as shown in FIG. 4k, for example.

Figure 5L:
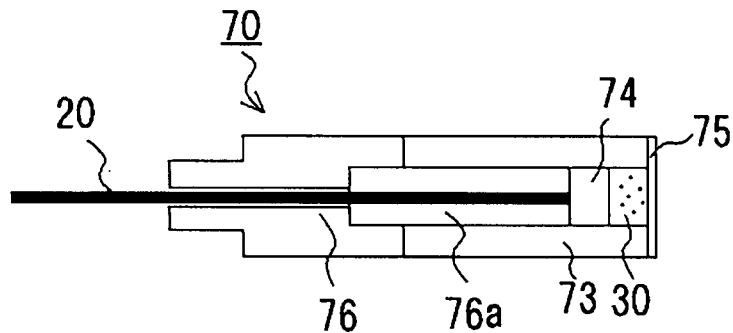
FIG. 5 is a simplified diagram illustrating the structure of still another light guide end portion in the light emitting device of the present invention.
Figure 5M:
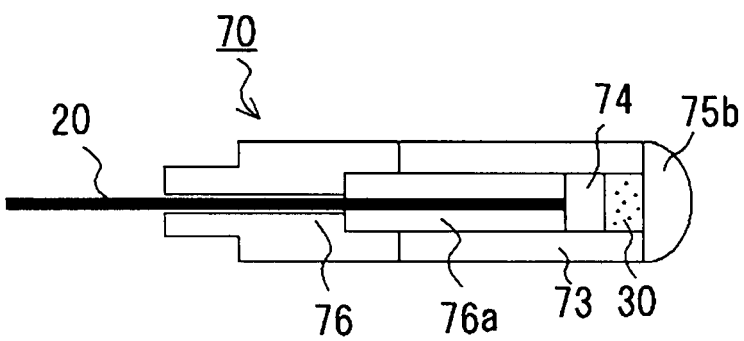
Figure 5N:
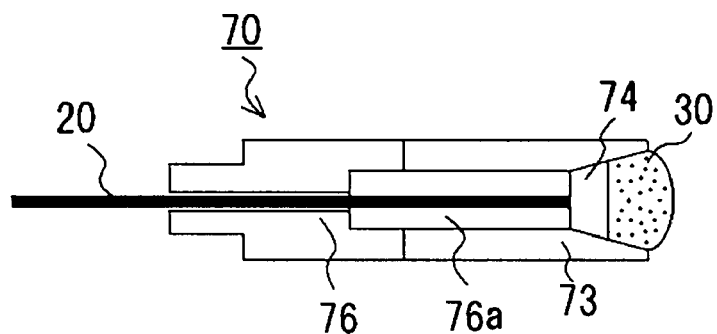
Figure 5O:
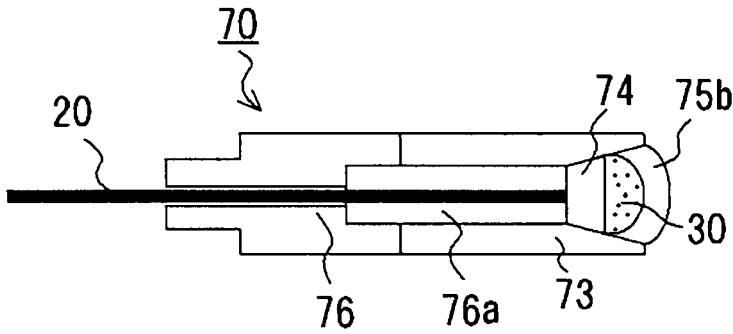

Also, as shown in FIG. 5o, the wavelength conversion member 30 can be formed by forming a conductive film of ITO or the like, and then selectively depositing a fluorescent material by electrodeposition coating, for example. This prevents the service life from being shortened by deterioration of the resin, and further improves reliability.

Functional Films and Members

Even if the aforementioned light guide distal end member is not attached, the light emitting device of the present invention preferably has various functional films/members attached in appropriate locations. Examples of these functional films/members include for instance a wavelength converted light reflecting film, excitation light reflecting film, scatter preventing member, and scattering member or the like.

The wavelength converted light reflecting film prevents wavelength converted light from the wavelength conversion member from returning to the excitation light incidence side and also can be used to externally discharge by reflecting light which has returned to the excitation light incidence side. Therefore, the wavelength converted light reflecting film is preferably formed from a material which can transmit only certain wavelengths of light while reflecting certain wavelengths, or in other words, wavelength converted light. Thereby the light which returns to the excitation light incidence side can be reflected and the light emitting efficiency can be increased. Furthermore, the wavelength converted light reflecting film 71 is preferably located at least on the excitation light incidence region of the wavelength conversion member 30, as shown in FIGS. 3b and d for instance.

The excitation light reflecting film can be used to prevent the excitation light from radiating directly to the outside or to prevent the excitation light from leaking to unintended areas. Thereby, excitation light which has passed through the wavelength conversion member but was not wavelength converted by the fluorescent material or the like can be returned back to the wavelength conversion member in order to increase the light emitting efficiency. Therefore, the excitation light reflecting film is preferably formed from a material which allows transmission of only light of a specific wavelength which has been wavelength converted but reflects excitation light. Furthermore, the excitation light reflecting film 72 is preferably located at least on the wavelength converted light emission region of the wavelength conversion member 30, as shown in FIGS. 3b and d for instance. Thereby radiation of excitation light to the outside can be reduced and the light emitting efficiency can be increased.

The scatter preventing member can be used to prevent excitation light and/or wavelength converted light from scattering in unintended directions. Therefore, the scatter preventing member is preferably constructed with materials and shape which block 90% or more of the excitation light or the wavelength converted light. For instance, at the joint between the light guide and the wavelength conversion member, the scatter preventing member may placed between the light guide and the wavelength conversion member, or may be placed to surround the boundary region between the light guide and the wavelength conversion member (see 73 in FIGS. 4f to j), or may be placed to cover the outside surface of the wavelength conversion member except for the wavelength converted light emitting region.

The scattering member can be used to increase the light emitting efficiency by causing more of the excitation light to shine on the fluorescent material or the light of the wavelength conversion member primarily by scattering the excitation light. Therefore the scattering member is preferably placed between the light radiating port of the light guide and the wavelength conversion member (see 74 in FIG. 4h). The scattering member may be made from the aforementioned resins which have relatively high refractive index or the aforementioned resins with the aforementioned fillers for instance. Of these materials, a silicone resin is preferable. Thereby deterioration and discoloration of the covering member which constitutes the wavelength conversion member can be reduced since the density of light that is irradiated to the wavelength conversion member can be reduced and the load on the wavelength conversion member per unit area can be reduced. Therefore, emission efficiency and linearity as well as the maximum of the emission output can be improved.

Figure 14:
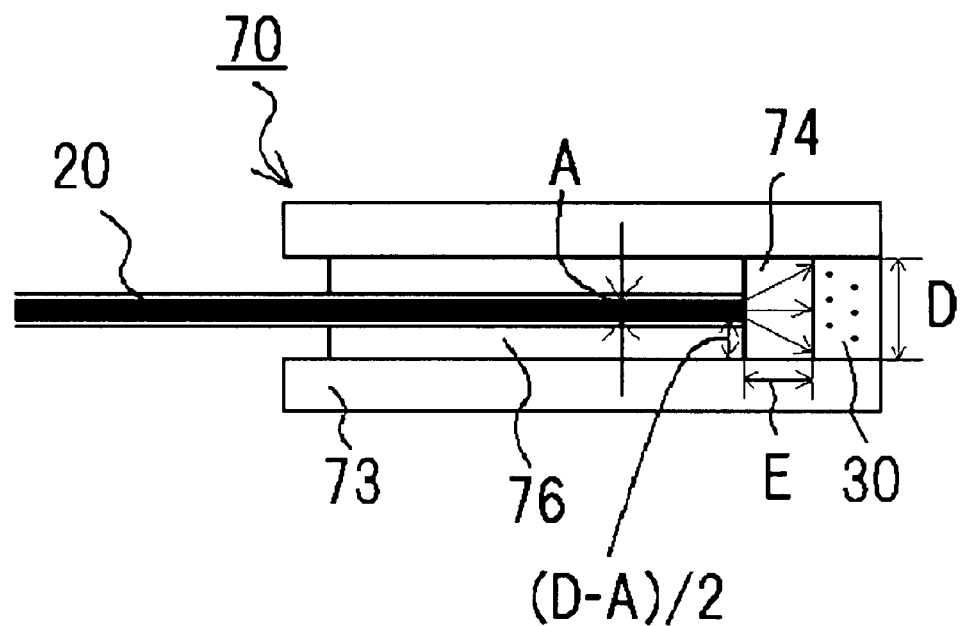
FIG. 14 is a cross-sectional diagram illustrating the thickness of the scattering member in the light emitting device of the present invention

For example, the thickness of the scattering member can be suitably adjusted by varying the core diameter of the light guide, the refractive index and thickness of the optional scattering member, the diameter of the wavelength conversion member, and so forth. More specifically, as shown in FIG. 14, if we let A be the core diameter of the light guide, B be the NA of the light guide (=n·sin θ), C be the refractive index n of the scattering member, D be the diameter of the wavelength conversion member, and E be the thickness of the scattering member, then the optimal value of the thickness E of the scattering member is calculated as follows.

$$E = \frac{\frac{(D-A)}{2}}{\tan\left(\sin^{-1}\frac{B}{C}\right)}$$ [First Numerical Formula]

Therefore, the thickness of the scattering member is preferably about ±20% of the thickness expressed by the above formula.

Shielding Member

The light emitting device of the present invention may also have a shielding member attached. The shielding member preferably shields 90% or more of the light from the excitation light source. Thereby only light of specific wavelengths may pass through. For instance, when using a light emitting element which radiates ultraviolet light which is harmful to humans, an ultraviolet light absorbing agent or reflecting agent or the like may be added to the wavelength conversion member in the light emitting region as a shielding member for shielding the ultraviolet rays. Therefore, emission of ultraviolet rays or the light can be suppressed. Using a reflecting agent is preferable over an absorbing agent from the viewpoint that the light emitting efficiency can be further increased.

Incidentally, the shielding member may also function as the aforementioned excitation light reflecting film or the scatter preventing film or the like so these materials may be used without strictly distinguishing.

Aspects of the Light Emitting Device

As shown in FIG. 1, the light emitting device of the present invention may be constituted by one excitation light source 10, one light guide 20, and one wavelength conversion member 30, and a plurality of these unit light emitting devices may be mounted in a light emitting device.

Also, the configuration may be such that a single excitation light source is provided with a plurality of light guides and corresponding wavelength conversion members. Or, the configuration may be such that a single excitation light source is provided with a plurality of light guides and one wavelength conversion member that converts the wavelength of the light from these light guides. Furthermore, the configuration may be such that there are a plurality of excitation light sources, a corresponding plurality of light guides, and one wavelength conversion member that converts the light from these light guides. These light emitting devices may also be combined and used as a single light emitting device.

The light emitting device of the present invention preferably uses units which each have a brightness of approximately 120 lumens/mm$^2$ or higher.

Light Emitting Device Applications

The light emitting device of the present invention with can be used in a variety of applications. For instance, the device may be used as a normal lighting fixture or as automotive lighting (specifically a light source for headlamps and tail lamps or the like), or may be used as a device such as an endoscope for observing inside a living body and performing treatment during observation. Furthermore, the device may also be used as a fiber scope for observing inside extremely narrow or dark spaces such as inside an atomic reactor or inside the space of enclosed artifacts. The device may also be used as a light source for various vacuum devices in members where current leak and heating or the like are to be avoided. In addition, the device may be used as a light emitting device for use in regions where a point light source is required or where replacing a light source is difficult.

Therefore, this light emitting device can be used together with an imaging member (in other words an electronic component which converts an optical image to electronic signal (photoreceptor element)), specifically with an imaging element which uses a CCD (charge coupled device) or CMOS (CMOS image sensor), as well as with an image signal processing device which converts an electric signal to an image signal, an indicator for displaying the electronic signal or a measurement value or the like, a display which outputs an image signal and creates an image, and a computer which performs various processes and calculations. In particular, when using an imaging element as an imaging member, the optical image of the object being photographed can easily be handled.

For instance, a photoreceptor element (such as a photo diode or the like) may be established separate from the light emitting device, but may also be established in the light guide distal end member or around the light guide in close proximity to the laser elements in the excitation light source. Thereby the intensity of light generated from the laser elements can be measured by the photoreceptor element, and when the intensity of light is below a fixed level, the current supplied to the laser element can be adjusted in order to maintain a fixed intensity of light.

The light emitting device of the present invention has high luminance with minimal color variation, extremely good color reproduction, and/or excellence color rendering properties, and therefore displays excellent effects for use in devices which require brilliant images or the like such as endoscope devices.

Furthermore, the light emitting device of the present invention can also be used for visible light communication. In other words, a wireless environment can be created by using visible light obtained from the aforementioned light emitting device and adding communication functions to the light emitting device. Thereby modulation speeds of several hundred MHz can be achieved because a laser element is used as the excitation light source.

Specific examples of the light emitting device of the present invention will be described in detail based on the figures.

Example 1

As shown in FIG. 1, this light emitting device comprised an excitation light source 10, a light guide 20, and a wavelength conversion member 30.

A light emitting element 11 which is a laser diode composed of a GaN-based semiconductor having an emission peak wavelength near 405 nm was used as the excitation light source 10. A lens 13 for converging excitation light 1 from the laser diode was disposed on the front face of this laser diode.

The light guide 20 was connected at one end to the emission portion 12 of the excitation light source 10, and connected at the other end to the output portion 21. The light guide 20 used here was an SI-type, made of quartz, with a core diameter of 114 μm and a cladding diameter of 125 μm.

The wavelength conversion member 30 was molded such that the fluorescent substance would be uniformly dispersed in the resin, and was attached to the output portion 21.

The fluorescent substance was a combination of $Ca_{10}(PO_4)_6Cl_2$:Eu (CCA) that emitted blue light, $Lu_3Al_5O_{12}$:Ce (LAG) that emitted green light, and $(Ca,Sr)_2Si_5N_8$:Eu (SCESN) that emitted red light, with these three used in a weight ratio of 0.7:0.28:0.02. These fluorescent substances were kneaded in a silicone resin until uniform. The weight ratio of the resin and fluorescent substance here was 1:1. Also, this wavelength conversion member 30 was produced by mixing into the resin a diffusion agent (such as an $SiO_2$ filler) for diffusing the light (near 405 nm) emitted from the laser diode (weight ratio of resin to filler=10:1). The thickness of the wavelength conversion member 30 in this case was about 500 μm.

Figure 6:
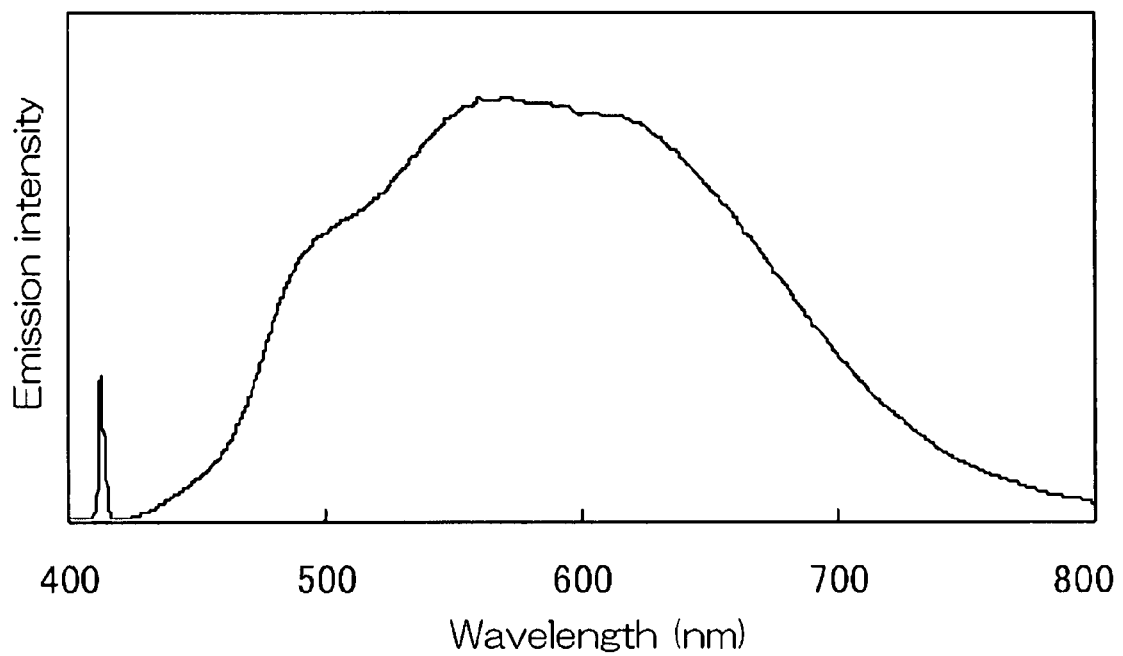
FIG. 6 is a plot of the emission spectrum of the light emitting device of Example 1.

With this light emitting device, the excitation light 1 emitted from the laser diode was transmitted through the lens 13 and converged at the emission portion 12. The converged excitation light 1 was transmitted through the light guide 20 to the output portion 21. The excitation light 1 guided out of the output portion 21 was directed at the fluorescent substance of the wavelength conversion member 30 and its wavelength was converted, so that light 2 having the emission spectrum shown in FIG. 6 was obtained.

This light 2 was emitted as white light, having a high special color rendering index (R9) indicating a red color chart, with the average color rendering index (Ra) being 80 or higher.

Thus, a light emitting device was obtained that had good color rendering properties and extremely little color tone variance, and that emitted light with excellent color reproducibility.

Example 2

With this light emitting device, two types of fluorescent substance were used, CCA and YAG. Each fluorescent substance was uniformly mixed with a resin. The wavelength conversion member that was used had a three-layer structure in which YAG, CCA, and YAG were laminated in that order, starting from the side closest to the excitation light. The distal end of the light guide was supported by a light guide distal end member, and the wavelength conversion member was disposed so as to integrally cover both the light guide and the light guide distal end member, but other than the above, the structure was the same as that of the light emitting device in Example 1.

Each fluorescent substance and the resin were mixed in a ratio of 2:1, and the thickness of each layer was about 100 μm.

Using this structure allowed the desired white light to be obtained, and a light emitting device with high emission efficiency was obtained by combining with a light emitting element having an emission peak wavelength at 400 nm.

The CCA here was excited by light from the excitation light source, while the YAG was excited by light from the CCA, and the YAG was substantially not excited by light from the excitation light source. In this Example, color change and deterioration of the wavelength conversion member can be reduced by disposing at least a first layer having YAG as a first fluorescent substance, and a second layer having CCA as a second fluorescent substance, starting from the side closest to the excitation light source.

In other words, first of all, since the first fluorescent substance is substantially not excited by the excitation light from the excitation light source, the excitation light tends not to generate heat, and furthermore the excitation light from the excitation light source can be scattered to decrease the optical density. Second, since the second fluorescent substance is excited upon receiving excitation light whose density has been decreased by the first fluorescent substance, it tends not to generate heat, allowing wavelength conversion to be accomplished more effectively. Third, since the first fluorescent substance is excited by low-density light from the second fluorescent substance, it tends not to generate heat, allowing wavelength conversion to be accomplished more effectively. Accordingly, the wavelength conversion member as a whole is capable of more effective wavelength conversion, and deterioration and color change can be reduced.

With this Example, the first fluorescent substance is disposed on the outside, rather than having the first fluorescent substance and the second fluorescent substance disposed in that order from the side closest to the excitation light source. This is preferable because the wavelength of the light from the second fluorescent substance can be converted more effectively.

Example 3

As shown in FIG. 1, this light emitting device comprised a excitation light source 10, a light guide 20, and a wavelength conversion member 30. The excitation light source 10 and the light guide 20 were the same as in Example 1. The wavelength conversion member 30 comprised a fluorescent substance 31 of $BaMg_2Al_{16}O_{27}$:Eu,Mn in silicone resin, mixed in a weight ratio of 1:1, kneaded until uniform, and molded.

Figure 7:
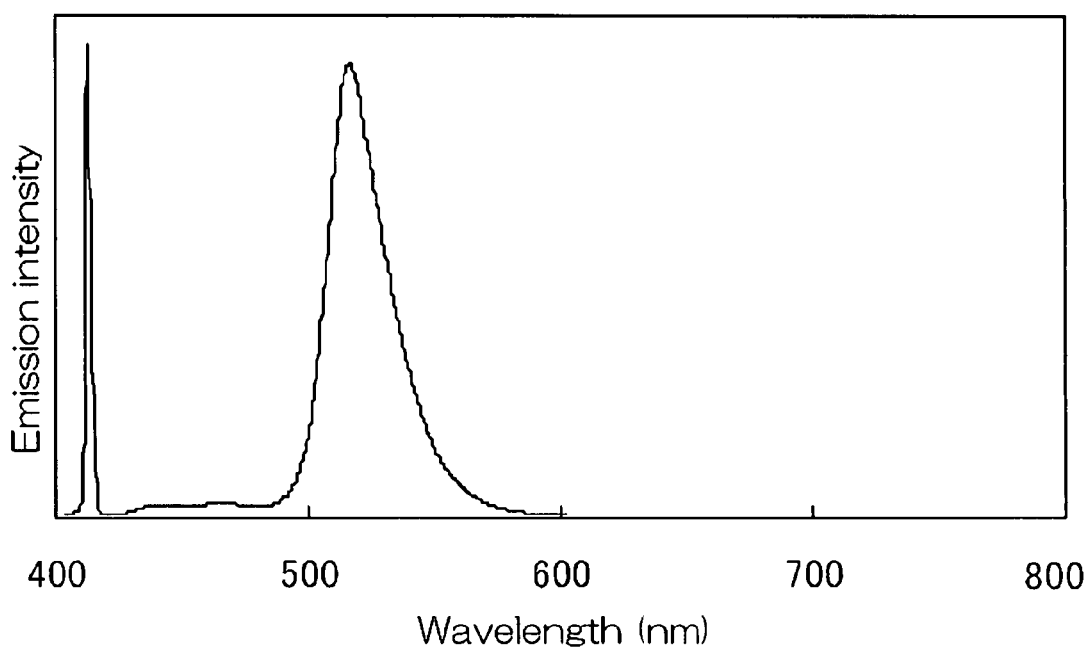
FIG. 7 is a plot of the emission spectrum of the light emitting device of Example 3.

With a light emitting device with this structure, the excitation light 1 emitted from the laser diode was transmitted through the lens 13 and converged at the emission portion 12. The converged excitation light 1 was transmitted through the light guide 20 to the output portion 21. The excitation light 1 guided out of the output portion 21 was directed at the fluorescent substance of the wavelength conversion member 30 and its wavelength was converted, so that light 2 having the emission spectrum shown in FIG. 7 was obtained.

This light was emitted as green light, and a light emitting device was obtained that emitted light with excellent color tone.

Example 4

Figure 8:
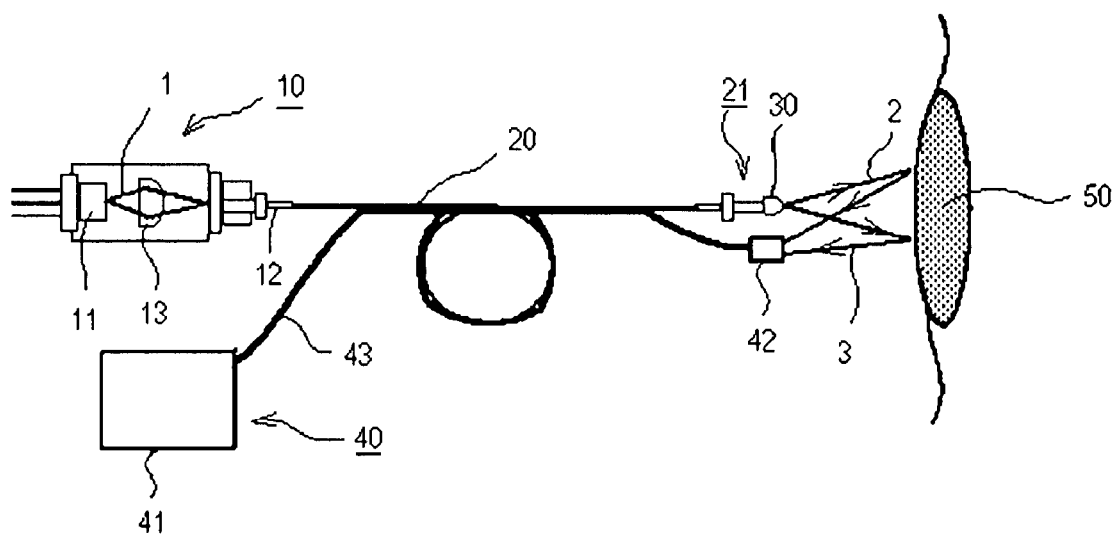
FIG. 8 is a simplified diagram illustrating an endoscope device in which the light emitting device of the present invention is used.

The light emitting device of the present invention can be utilized as an endoscope device as shown in FIG. 8, for example.

This endoscope device is made up primarily of the light emitting device obtained in Example 1 or 2 and an image capture component 40 that directs the light emitted from the light emitting device at an internal organ or other subject, and captures an ordinary image produced by light reflected by the subject. The image capture component 40 is made up of an image signal processor 41, a cable 43 that is connected at one end to the image signal processor 41 in order to transmit signals to the image signal processor 41, and a camera 42 mounted at the other end of this cable. An image capture element that converts optical images into electrical signals is provided inside the camera 42.

With this endoscope device, the excitation light 1 emitted from the laser diode is transmitted through the lens 13 and converged at the emission portion 12. The converged excitation light 1 is transmitted through the light guide 20 to the output portion 21. The excitation light 1 guided out of the output portion 21 is directed at the fluorescent substance of the wavelength conversion member 30 and its wavelength is converted, so that light 2 is released to the outside.

The released light 2 is directed at the afflicted part of a patient, subject 50. Part of the light directed at the subject 50 is absorbed, and part is reflected. The reflected light 3 is captured as an optical image by the image capture element inside the camera 42, and the image signal corresponding to the optical image is converted into an electrical signal. The electrical signal is transmitted through the cable 43 to the image signal processor 41, signal processing in the signal processing circuit of the image signal processor 41 produces a video signal from the electrical signal, and this is outputted to a television monitor, which displays an endoscopic image of the afflicted site.

The camera 42 equipped with the image capture element is mounted so that it can move substantially integrally with the output portion 21 of the light emitting device, so that the light 2 emitted from the output portion 21 will not be directly incident on the image capture element. This allows an endoscope device to be obtained that has good color rendering properties and extremely little color tone variance, and that utilizes light with excellent color reproducibility to observe and diagnose a suitable afflicted site.

Example 5

Figure 9:
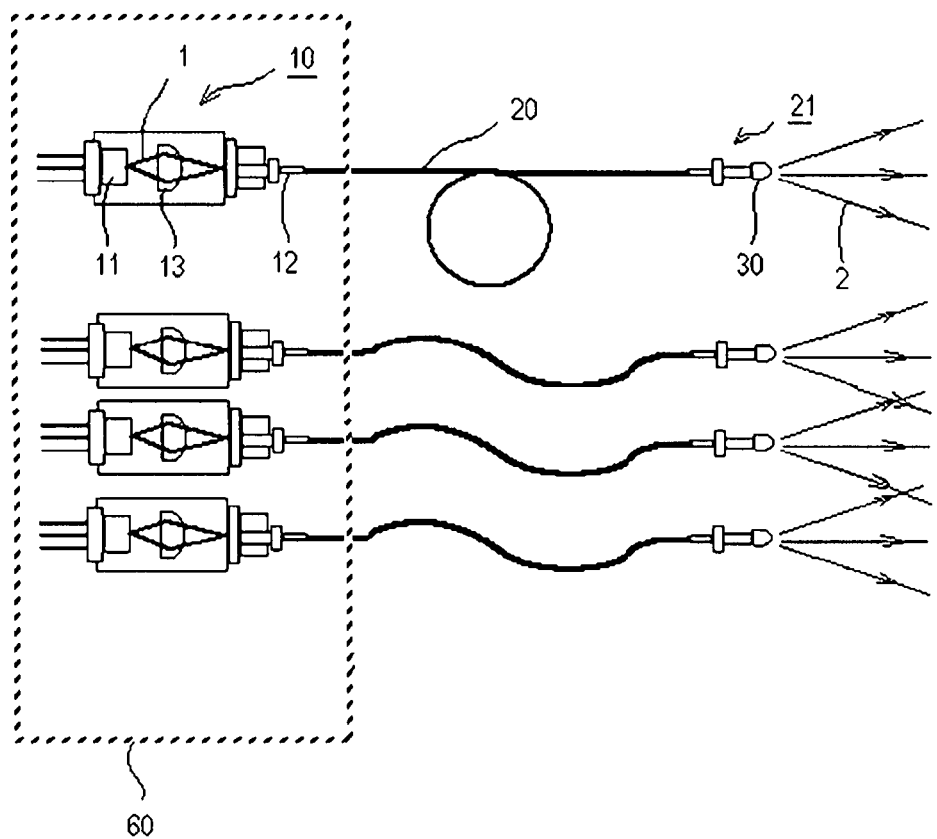
FIG. 9 is a simplified diagram illustrating the light emitting device of Example 5 of the present invention.

As shown in FIG. 9, for example, the light emitting device of the present invention comprises a plurality of unit light emitting devices, each composed of the excitation light source 10, the light guide 20, and the wavelength conversion member 30. An electronic circuit (not shown) is connected to each of the excitation light sources 10, and this electronic circuit is used to switch the power to the excitation light source 10 on and off, and to control the amount of power coming in to the device.

The wavelength conversion members 30 are formed, for example, so as to emit the three primary colors of blue, green, and red, and various other kinds of colors, and the desired white light can be obtained by combining the light of these colors.

Also, if a plurality of units is used, brightness corresponding to the number of used units can be ensured.

Example 6

Figure 10:
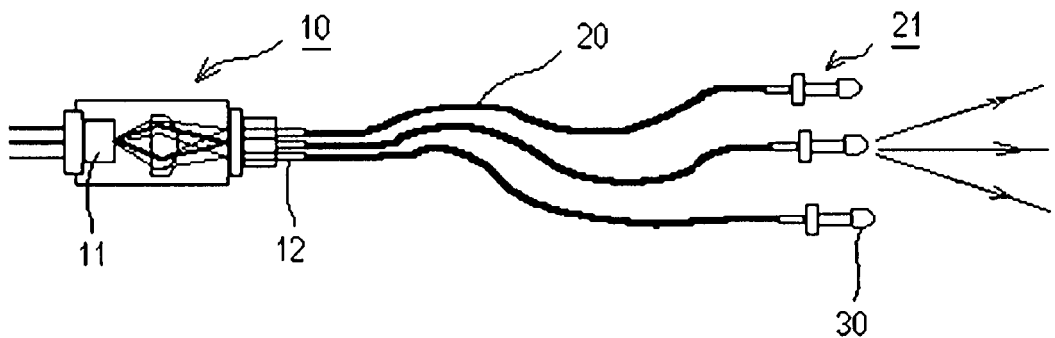
FIG. 10 is a simplified diagram illustrating the light emitting device of Example 6 of the present invention.

As shown in FIG. 10, for example, the light emitting device of the present invention comprises one excitation light source 10, a plurality of light guides 20 connected at one end to the one excitation light source 10, and a wavelength conversion member 30 attached to the other ends of the light guides. A lens is disposed in front of the light emitting element in the excitation light source 10.

With this configuration, the excitation light emitted from the light emitting element is converged by the lens and sent to the emission portion 12. Therefore, if the lens 13 is able to move, excitation light will be sent to any one of the plurality of emission portions 12 provided at specific locations. The excitation light 1 that comes in passes through the light guides 20 and is directed at the fluorescent substance 31, and the light 2 is released to the outside. This allows the excitation light 1 to be sent to a plurality of light guides by a single excitation light source 10.

Example 7

Figure 11:
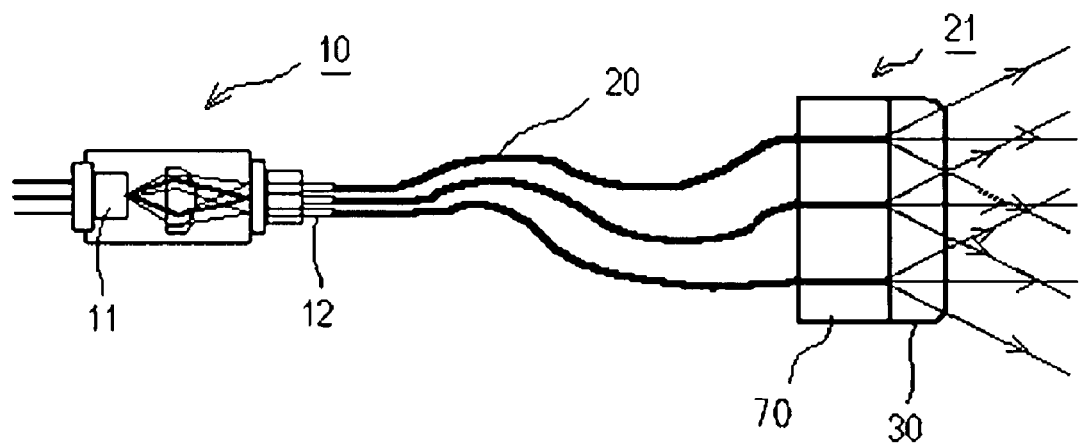
FIG. 11 is a simplified diagram illustrating the light emitting device of Example 7 of the present invention.

As shown in FIG. 11, for example, the light emitting device of the present invention comprised one excitation light source 10, a plurality of light guides 20, and a wavelength conversion member 30. The plurality of light guides 20 are all connected at one end to the single excitation light source 10, and integrally supported at the other end by the light guide distal end member 70. Also, the one wavelength conversion member 30, which covers the light exits of the light guides 20 and also embeds these light exits, is attached to the end face of the light guide distal end member 70.

When excitation light is thus directed at the wavelength conversion member from a plurality of locations, the density of excitation light emitted from a single light guide exit can be reduced although the output is high. Also, if a plurality of light guides is disposed separated from each other by a certain distance, the excitation light can be guided to the wavelength conversion member without waste, allowing the light to be emitted more efficiently.

Example 8

Figure 12:
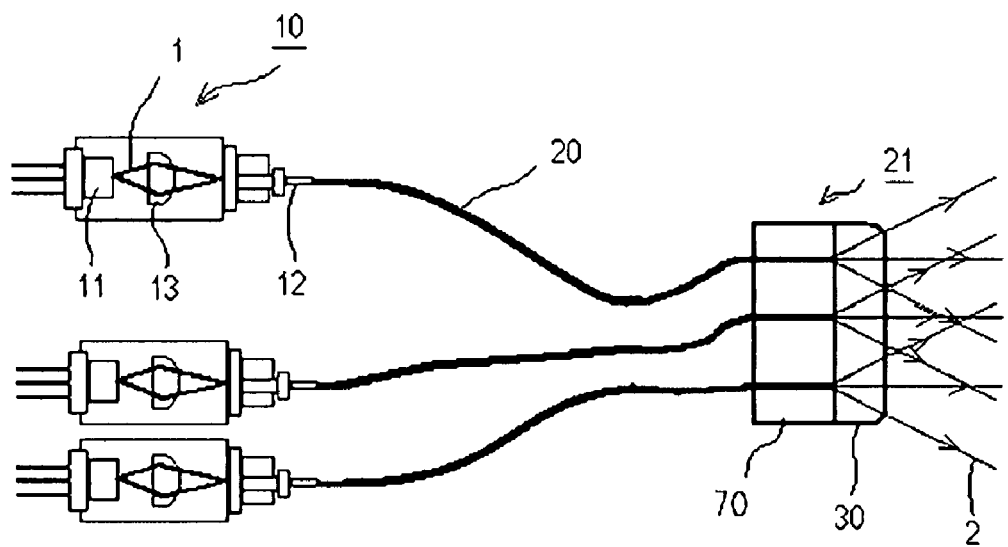
FIG. 12 is a simplified diagram illustrating the light emitting device of Example 8 of the present invention.

As shown in FIG. 12, for example, the light emitting device of the present invention comprised three excitation light sources 10, a plurality of light guides 20, and a wavelength conversion member 30. The plurality of light guides 20 are each connected at one end to one of the single excitation light sources 10, and integrally supported at the other end by the light guide distal end member 70. Also, the one wavelength conversion member 30, which covers the light exits of the light guides 20 and also embeds these light exits, is attached to the end face of the light guide distal end member 70.

When excitation light is thus directed at the wavelength conversion member 30 from a plurality of locations, the density of excitation light emitted from a single light guide exit can be reduced although the output is high. This affords a reduction in the deterioration of the wavelength conversion member. Also, if a plurality of light guides is disposed separated from each other by a certain distance, the excitation light can be guided to the wavelength conversion member without waste, allowing the light to be emitted more efficiently.

Example 9

This light emitting device was produced in substantially the same manner as the light emitting device in Example 1, except that a light emitting element (laser diode) composed of a GaN-based semiconductor having an emission peak wavelength near 445 nm was used as the excitation light source, 0.54 g of $Lu_3Al_5O_{12}$:Ce (LAG) that emitted green light, 0.02 g of $(Ca,Sr)_2Si_5Ng$:Eu (SCESN) that emitted red light, and 1.1 g of silicone resin were used for the wavelength conversion member, and a plurality of samples were produced in which the contact surface area between the wavelength conversion member and the light guide and light guide distal end member was varied. Also, for the sake of comparison, a light emitting device was produced in which no wavelength conversion member was disposed. The relationship of the wavelength conversion member 30 to the light guide 20 and the light guide distal end member 70 (made of zirconia) shown in FIG. 3a was employed as FIG. 15A (shown below) in this light emitting device.

Figure 15:
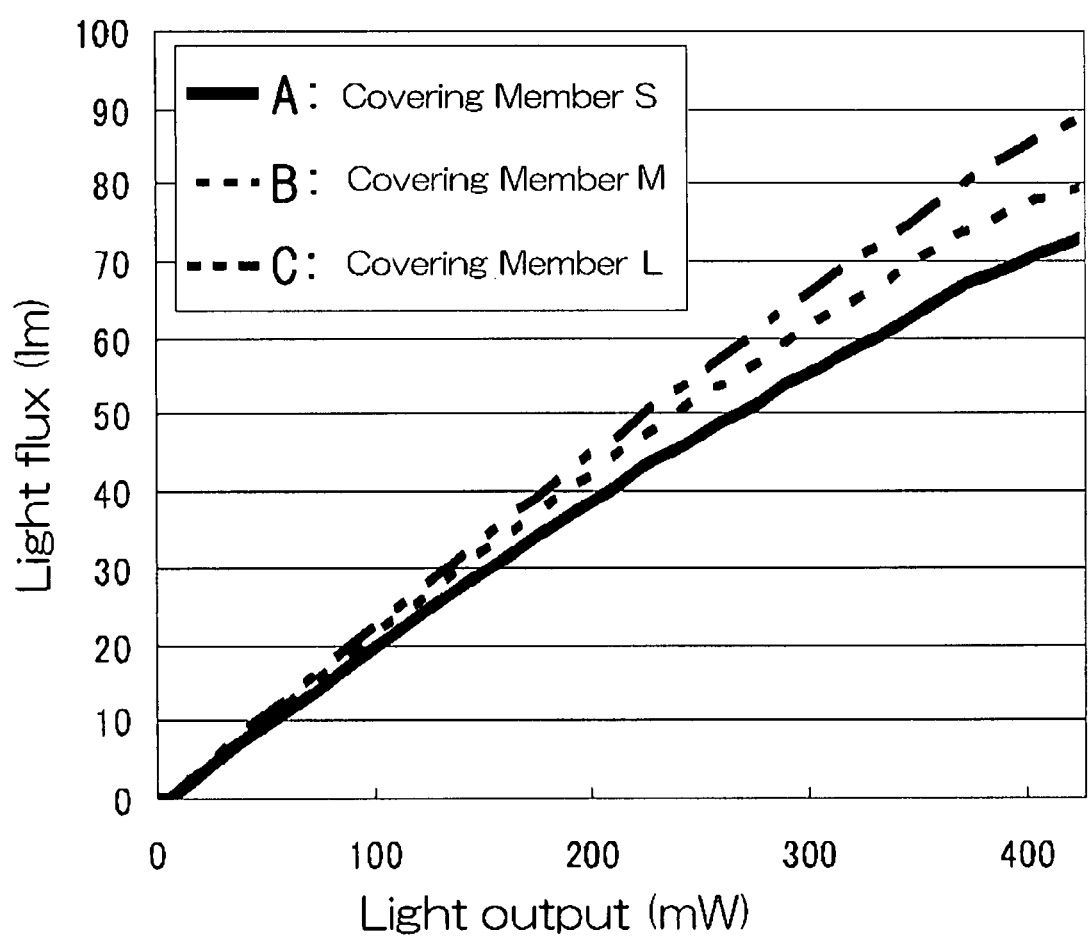
FIG. 15 is a graph of the relationship between the light flux and light output of the light emitting device of the present invention.

The relationship between light flux and light output was measured for these light emitting devices, the results of which are given in FIG. 15. In FIG. 15, the horizontal axis shows the light output, at a specific current flow, of a light emitting device with no wavelength conversion member, the vertical axis shows the light flux of a light emitting device with a wavelength conversion member, and the graph shows the degree of difference between the two. A to C in FIG. 15 are all cases in which the light guide is covered, with the region in which the light guide distal end member is covered increasing from A to C. More specifically, A is a case in which the light guide is mainly covered, C is a case in which substantially all of the light guide distal end member is covered, and B is in between these two.

In FIG. 15, the light flux increases markedly in proportion to the contact surface area between the wavelength conversion member and the light guide and light guide distal end member. The deterioration, i.e., discoloration of the resin which constitutes the wavelength conversion member reduced in proportion to increase of the contact surface area. More specifically, the light flux value at which the color of the resin changed was greatest with C, then B and then A. The reason for this seems to be that as the contact surface area between the wavelength conversion member and the light guide distal end member increases, mainly light that has undergone wavelength conversion is reflected by the light guide distal end member, and there is an increase in heat radiation from the wavelength conversion member to the light guide distal end member.

Furthermore, a case in which a wavelength conversion member composed of a covering member and a fluorescent substance was described in this Example, but a light emitting device that is the same as in this Example can also be obtained by removing the fluorescent substance from the wavelength conversion member. That is, it is possible to use not only a translucent member that includes a fluorescent substance, but also a translucent member that does not contain a fluorescent substance. Even in this case, the constitution of this Example affords an increase in the light flux of the light emitting device.

Specifically, the translucent member transmits light from the light source, but part of the light absorbed by the fluorescent substance does not undergo wavelength conversion and turns into heat, and similarly, when just a translucent member is provided, part of the light from the light source is not transmitted through the translucent member, and is instead absorbed and turns into heat. With the constitution discussed above, however, heat can be efficiently allowed to escape from the translucent member to the light guide distal end member, and this reduces discoloration and deterioration of the translucent member caused by heat.

Example 10

With this light emitting device, a light emitting element (laser diode) composed of a GaN-based semiconductor having an emission peak wavelength near 445 nm was used as the excitation light source.

The wavelength conversion member was composed of a first layer containing $Lu_3Al_5O_{12}$:Ce (LAG) that emitted green light (as the first fluorescent substance), and a second layer that contained $CaAlSiB_{0.1}N_{2.9}$ (CASBN) that emitted red light (as the second fluorescent substance), with a silicone resin covering member. The first layer and second layer were disposed in that order starting from the side closest to the excitation light source. The first layer was formed by the potting of the product of adding 0.53 g of LAG to 1.1 g of silicone resin. The second layer was formed by the potting of the product of adding 0.045 g of CASBN to 1.1 g of silicone resin (the same type as in the first layer). The first fluorescent substance was excited by light from the excitation light source, while the second fluorescent substance was excited by light from the first fluorescent substance.

Figure 16:
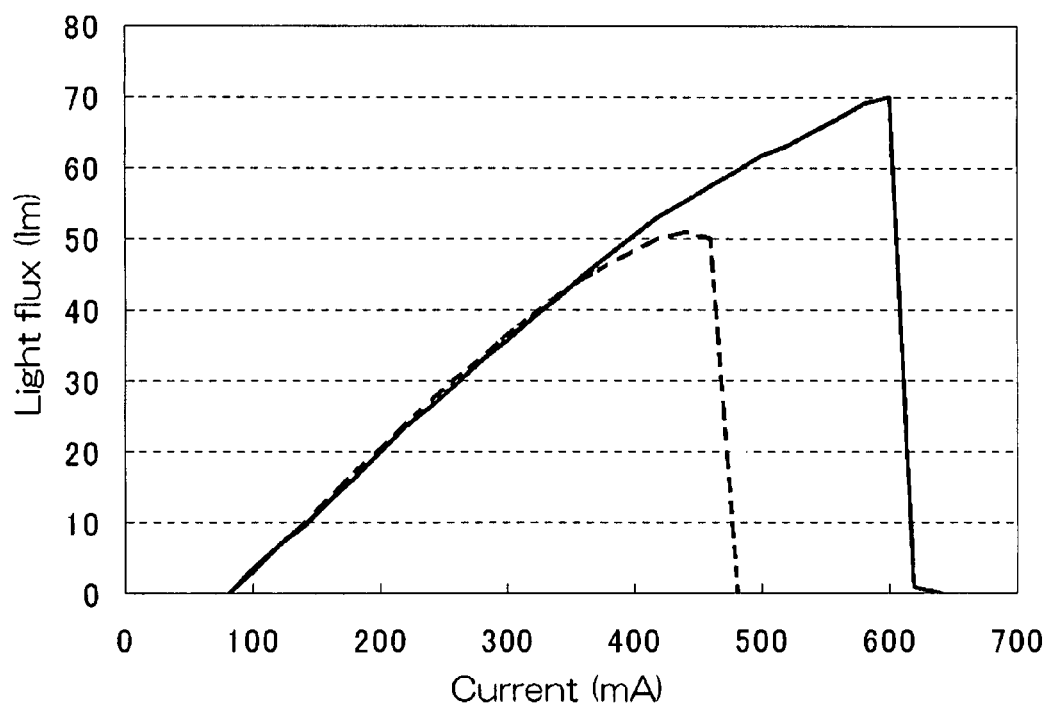
FIG. 16 is a graph of the relationship between the light flux and current of the light emitting device of the present invention.
Figure 17:
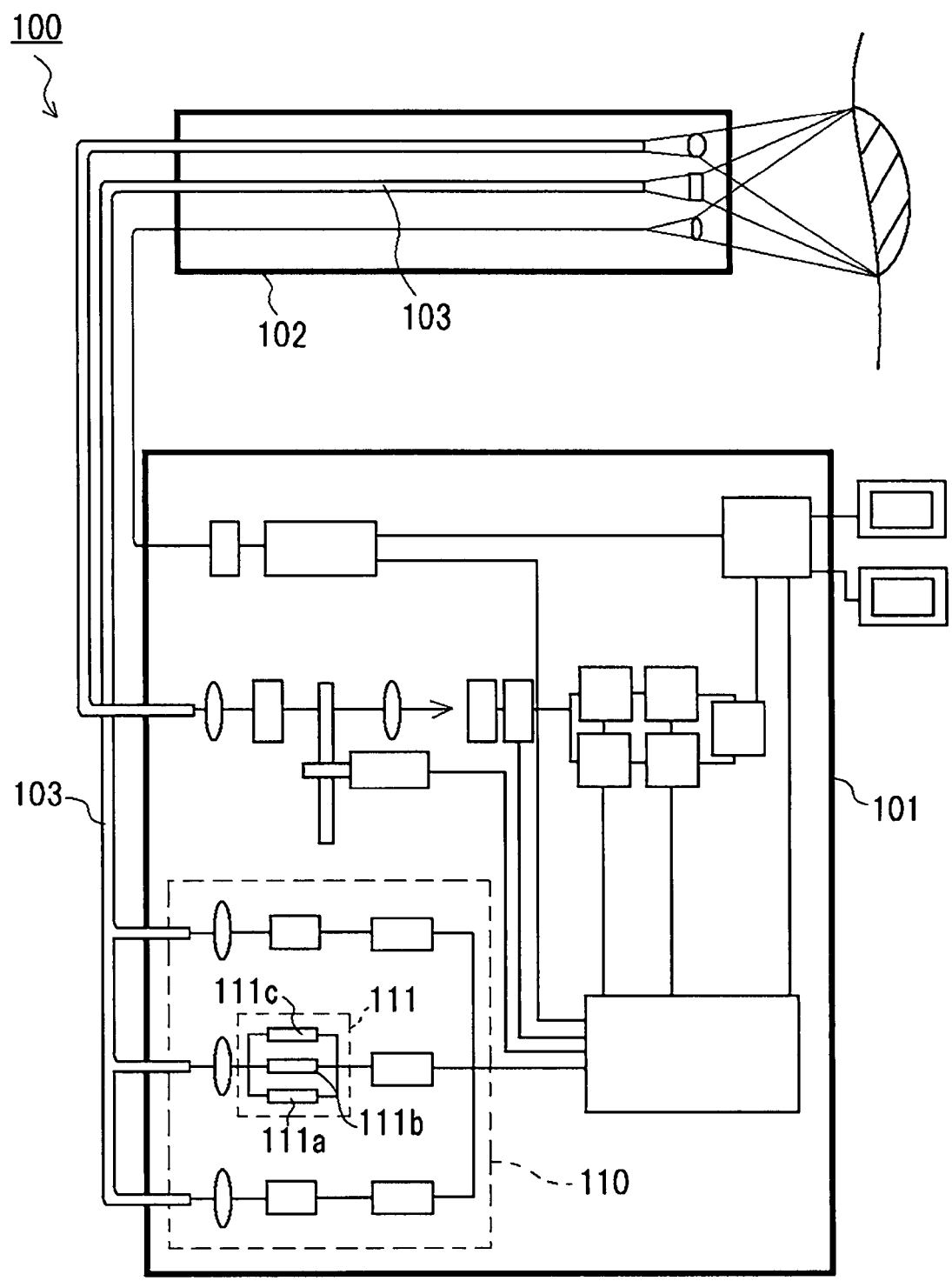
FIG. 17 is a simplified diagram illustrating the conventional light emitting device.

The laser diode with this constitution was driven at 80 to 640 mA and its characteristics were evaluated, the results of which are indicated by the solid line in FIG. 16.

As a comparative example, a light emitting device was produced in the same manner as in this Example, except that 0.53 g of LAG (first fluorescent substance) and 0.045 g of CASBN (second fluorescent substance) were mixed with 1.1 g of silicone resin (covering material), and this product was potted to form a single layer of the wavelength conversion member. The characteristics of the laser diode in this comparative example were evaluated in the same way as above, the results of which are indicated by the broken line in FIG. 16.

As shown in FIG. 16, it was confirmed that the light emitting device of this Example had a maximum light flux that was about 40% higher than that of the light emitting device in the comparative example. Meanwhile, with the light emitting device of the comparative example, the light flux decreased suddenly when the drive current reached about 440 mA. The main reason for this is that the covering material (silicone resin) constituting the wavelength conversion member was degraded and discolored by heat. In contrast, in the Example, it was confirmed that the light flux increased without reaching a saturation point up to a drive current of about 600 mA. It can be seen from the above results that with the light emitting device of this Example, the covering material was less likely to deteriorate than in the comparative example.

What increases the maximum light flux value with the light emitting device in this Example is that the first fluorescent substance, which produces less heat, was disposed on the side closest to the excitation light source, and the second fluorescent substance, which produced more heat, was disposed on the side farther away from the excitation light source. That is, the degradation of the covering member by heat can be effectively reduced by moving the second fluorescent substance, which produces more heat, farther away from the excitation light source. Also, since the first fluorescent substance contained in the first layer scatters light and decreases the optical density, the generation of heat by the second fluorescent substance in the second layer can be reduced.

Example 11

A light emitting device with the same constitution as in Examples 1 and 2 was produced, except that the wavelength conversion member was disposed at the emission portion between the light guide and the excitation light source.

Example 12

A light emitting device with the same constitution as in Examples 1 and 2 was produced, except that the light guide was supported by the light guide distal end member 70 shown in FIG. 3a, which was composed of $ZrO_2$.

All of the light emitting devices thus obtained were similar to those of Examples 1 and 2 in that the color rendering properties were good, there was extremely little variance in color tone, and light with excellent color reproducibility was emitted. Also, the deterioration of the wavelength conversion member was effectively prevented.

Example 13

A light emitting device with the same constitution as in Examples 1 and 2 was produced, except that the light guide had the constitution shown in FIG. 13a.

All of the light emitting devices thus obtained were similar to those of Examples 1 and 2 in that the color rendering properties were good, there was extremely little variance in color tone, and light with excellent color reproducibility was emitted. Also, the deterioration of the wavelength conversion member was effectively prevented.

Example 14

A light emitting device with the same constitution as in Examples 1 and 2 was produced, except that the light guide was supported by the light guide distal end member 70 shown in FIG. 3d, which was composed of $ZrO_2$, and the wavelength-converted light reflecting film 71 and excitation light reflecting film 72 were disposed before and after the wavelength conversion member.

All of the light emitting devices thus obtained were similar to those of Examples 1 and 2 in that the color rendering properties were good, there was extremely little variance in color tone, and light with excellent color reproducibility was emitted. Also, the deterioration of the wavelength conversion member was effectively prevented.

Example 15

A light emitting device with the same constitution as in Examples 1 and 2 was produced, except that the light guide was supported by the light guide distal end member 70 shown in FIG. 4g, which was composed of $ZrO_2$, and the scatter preventing member 73 was disposed only on the surface on the lateral face side of the wavelength conversion member.

Example 16

A light emitting device with the same constitution as in Examples 1 and 2 was produced, except that the end face of the light guide on the wavelength conversion member side had a mirror finish or an uneven texture.

All of the light emitting devices thus obtained in Examples 11 to 16 were similar to those of Examples 1 and 2 in that the color rendering properties were good, there was extremely little variance in color tone, and light with excellent color reproducibility was emitted. Also, with the light emitting devices obtained in Examples 12 to 15, the deterioration of the wavelength conversion member was effectively prevented.

INDUSTRIAL APPLICABILITY

The light emitting device of the present invention with can be utilized in projector devices, lighting fixture, automotive lighting, laser display, indicator, and so forth. Furthermore, the device may also be utilized as an endoscope for observing inside a living body, as a fiber scope for observing inside extremely narrow or dark spaces, and as a light source for various industrial, constructions in members where current leak and heating or the like are to be avoided.

What is claimed is:

1. A light emitting device, comprising:
   an excitation light source that emits excitation light;
   a wavelength conversion member that absorbs the excitation light emitted from the excitation light source, converts its wavelength, and releases light of a predetermined wavelength band; and
   a light guide in which the center part of its cross section has a refractive index that is higher than the refractive index of the peripheral portion, and which guides the excitation light emitted from the excitation light source to the wavelength conversion member,
   wherein the wavelength conversion member being produced by laminating a plurality of layers that convert different wavelengths of light.

2. The light emitting device according to claim 1, wherein the distal end of the light guide on the wavelength conversion member side is supported by a light guide distal end member, and the light guide distal end member is formed from a material that reflects at least one of the excitation light and the light that has undergone wavelength conversion.

3. The light emitting device according to claim 2, wherein the wavelength conversion member, along with the end of the light guide, covers all or part of the end of the light guide distal end member.

4. The light emitting device according to claim 2, wherein at least one of the light guide distal end member and the light guide has an end face for mirror surface reflection or scattered reflection, or an end face that has an uneven surface.

5. The light emitting device according to claim 1, wherein the light guide is such that the diameter of the center part of its cross section is formed larger only at the end on the wavelength conversion member side.

6. The light emitting device according to claim 1, further comprising at least one of
   a wavelength-converted light reflecting film provided to the portion of the wavelength conversion member into which excitation light is guided, and
   an excitation light reflecting film provided to the portion of the wavelength conversion member from which wavelength-converted light is guided.

7. The light emitting device according to claim 1, wherein a scatter preventing member is formed at least one of between the wavelength conversion member and the light guide, and on the surface of the wavelength conversion member except for the portion from which wavelength-converted light is guided to the outside.

8. The light emitting device according to claim 1, comprising a plurality of light guides.

9. The light emitting device according to claim 1, further comprising a lens between the excitation light source and the light guide, wherein the excitation light emitted from the excitation light source is guided into the light guide via the lens.

10. The light emitting device according to claim 1, further having a shielding member that blocks at least 90% of the light from the excitation light source.

11. The light emitting device according to claim 1, wherein the wavelength conversion member has, from the side closest to the excitation light source, at least a first layer having a first fluorescent substance, and a second layer having a second fluorescent substance,
    the second fluorescent substance is excited by the excitation light from the excitation light source, and
    the first fluorescent substance is excited by light from the second fluorescent substance.

12. The light emitting device according to claim 1, wherein the wavelength conversion member has, from the side closest to the excitation light source, at least a first layer having a first fluorescent substance, and a second layer having a second fluorescent substance,
    the first fluorescent substance produces less heat caused by excitation light than that of the second fluorescent substance.

13. A light emitting device comprising:
    an excitation light source that emits excitation light;
    a wavelength conversion member that absorbs the excitation light emitted from the excitation light source, converts its wavelength, and releases light of a predetermined wavelength band; and
    a light guide in which the center part of its cross section has a refractive index that is higher than the refractive index of the peripheral portion, and which guides the excitation light emitted from the excitation light source to the wavelength conversion member,
    the wavelength conversion member being made of a mixture of two or more types of fluorescent materials.

14. The light emitting device according to claim 13, wherein the wavelength conversion member includes one of a combination of $(Sr,Ca)_5(PO_4)_3Cl:Eu$, one of LAG and $BaSi_2O_2N_2:Eu$, and SCESN, a combination of YAG and one of CCA, CCB and BAM, and a combination of one of CCA, CCB and BAM, LAG, and SCESN arranged in this order from the light incidence side.

15. The light emitting device according to claim 13, wherein the fluorescent materials include at least one of
$Y_3Al_5O_{12}$:Ce,
$(Y_{0.8}Gd_{0.2})_3Al_5O_{12}$:Ce,
$Y_3(Al_{0.8}Ga_{0.2})_5O_{12}$:Ce,
$(Y,Gd)_3(Al,Ga)_5O_{12}$:Ce,
$Y_3(Al,Sc)_5O_{12}$:Ce,
$Lu_3Al_5O_{12}$:Ce,
$Tb_3Al_5O_{12}$:Ce, and
$Gd_3(Al,Ga)_5O_{12}$:Ce.

16. The light emitting device according to claim 13, wherein the fluorescent materials include a combination of YAG and at least one of CCA, CCB and BAM.

17. The light emitting device according to claim 13, wherein the fluorescent materials have a particle size in the range of approximately 1 μm to 20 μm.

18. The light emitting device according to claim 13, wherein the wavelength conversion member contains a filler.

19. The light emitting device according to claim 13, wherein a scatter preventing member is formed at least one of between the wavelength conversion member and the light guide, and on the surface of the wavelength conversion member except for the portion from which wavelength-converted light is guided to the outside.

20. The light emitting device according to claim 14, wherein the excitation light source has a light emission peak wavelength within a range from 360 to 470 nm.

* * * * *